United States Patent
Weselake et al.

(10) Patent No.: US 8,148,602 B2
(45) Date of Patent: Apr. 3, 2012

(54) DIACYLGLYCEROL ACYLTRANSFERASES FROM FLAX

(76) Inventors: Randall Weselake, Edmonton (CA); Rodrigo Siloto, Edmonton (CA); Qin Liu, Edmonton (CA); André Laroche, Lethbridge (CA); Eric Murphy, Grand Forks, ND (US); Kimmo Koivu, Itasalmi (FI)

( * ) Notice: Subject to any disclaimer, the term of this patent is extended or adjusted under 35 U.S.C. 154(b) by 227 days.

(21) Appl. No.: 12/381,183

(22) Filed: Mar. 9, 2009

(65) Prior Publication Data

US 2009/0249516 A1   Oct. 1, 2009

Related U.S. Application Data

(60) Provisional application No. 61/034,787, filed on Mar. 7, 2008.

(51) Int. Cl.
| | |
|---|---|
| A01H 1/00 | (2006.01) |
| A01H 5/00 | (2006.01) |
| A01H 5/10 | (2006.01) |
| A01H 15/00 | (2006.01) |
| C12N 5/14 | (2006.01) |
| C12N 15/82 | (2006.01) |
| C07H 21/04 | (2006.01) |

(52) U.S. Cl. ........ 800/272; 800/281; 800/306; 800/312; 800/320; 800/320.1; 800/320.3; 800/322; 536/23.6; 435/254.11; 435/320.1; 435/419

(58) Field of Classification Search .................. None
See application file for complete search history.

(56) References Cited

U.S. PATENT DOCUMENTS

2009/0293152 A1* 11/2009 Roesler et al. ............... 800/281
* cited by examiner

*Primary Examiner* — Eileen B O Hara
(74) *Attorney, Agent, or Firm* — John Dodds

(57) ABSTRACT

The invention relates to isolated diacylglycerol acyltransferases and polynucleotide sequences encoding the DGAT enzymes; polynucleotide constructs, vectors and host cells incorporating the polynucleotide sequences; and methods of producing and using same. Also provided are transformed cells and transgenic plants, especially *Camelina sativa* plant, with enhanced oil accumulation and quality.

19 Claims, 18 Drawing Sheets

```
3'RACE      (1)
RT-PCR      (1)
amplicon1   (1)
amplicon2   (1)
5'RACE      (1)                                                               CGGTGCTCGACACCCCTGAC
5'RACEB     (2)  CTTTCGGTGTGTTATCATCGTTCTTTCTGCGACTGCTTCCCCCCTCTCCTCTTCCAATGGCGGTGCTCGACACCCCTGAC
Consensus   (2)  CTTTCGGTGTGTTATCATCGTTCTTTCTGCGACTGCTTCCCCCCTCTCCTCTTCCAATGGCGGTGCTCGACACCCCTGAC 3'RACE      (1)
RT-PCR      (1)
amplicon1   (1)
amplicon2   (1)
5'RACE     (23)  AATCACATAAACCCCTCTCCCTCCACCTCTGCTATTGACTCCTCCGATCTTAACGGTCTCTCCCTTCGACGTCGTTCAGT
5'RACEB    (82)  AATCACATAAACCCCTCTCCCTCCACCTCTGCTATTGACTCCTCCGATCTTAACGGTCTCTCCCTTCGACGTCGTTCAGT
Consensus  (82)  AATCACATAAACCCCTCTCCCTCCACCTCTGCTATTGACTCCTCCGATCTTAACGGTCTCTCCCTTCGACGTCGTTCAGT 3'RACE      (1)
RT-PCR      (1)
amplicon1   (1)
amplicon2   (1)
5'RACE    (103)  TGCCACTAACTCCGACCAAGGTACTTCTTCCACCGCTGTAGAATCACTCCACGCGGATCGGCCAGCCGATTCTGATGGGG
5'RACEB   (162)  TGCCACTAACTCCGACCAAGGTACTTCTTCCACCGCTGTAGAATCACTCCACGCGGATCGGCCAGCCGATTCTGATGGGG
Consensus (162)  TGCCACTAACTCCGACCAAGGTACTTCTTCCACCGCTGTAGAATCACTCCACGCGGATCGGCCAGCCGATTCTGATGGGG 3'RACE      (1)
RT-PCR      (1)
amplicon1   (1)
amplicon2   (1)
5'RACE    (183)  CGAACCGCGAGGATAAGAAGATTGACAATCGGGACGGTCAAGTTGCGAGATCGGATATCAAATTCACTTACCGCCCTTCC
5'RACEB   (242)  CGAACCGCGAGGATAAGAAGATTGACAATCGGGACGGTCAAGTTGCGAGATCGGATATCAAATTCACTTACCGCCCTTCC
Consensus (242)  CGAACCGCGAGGATAAGAAGATTGACAATCGGGACGGTCAAGTTGCGAGATCGGATATCAAATTCACTTACCGCCCTTCC 3'RACE      (1)
RT-PCR      (1)
amplicon1   (1)
amplicon2   (1)
5'RACE    (263)  GTGCCCGCTCACGTCAAGGTTAAAGAGAGTCCGCTTAGTTCCGGCGCCATTTTTAAGCAGAGCCATGCAGGCCTCTTCAA
5'RACEB   (322)  GTGCC
Consensus (322)  GTGCCCGCTCACGTCAAGGTTAAAGAGAGTCCGCTTAGTTCCGGCGCCATTTTTAAGCAGAGCCATGCAGGCCTCTTCAA 3'RACE      (1)
RT-PCR      (1)
amplicon1   (1)
amplicon2   (1)                                                   ATGAAGTATGGTTGGTTAATTAGGA
5'RACE    (343)  TCTCTGTATTGTAGTCCTAGTTGCAGTCAACAGCAGGCTTATTATCGAGAATATCATGAAGTATGGTTGGTTAATTAGGA
5'RACEB   (325)
Consensus (402)  TCTCTGTATTGTAGTCCTAGTTGCAGTCAACAGCAGGCTTATTATCGAGAATATCATGAAGTATGGTTGGTTAATTAGGA 3'RACE      (1)
RT-PCR      (1)
amplicon1   (1)
amplicon2  (28)  CAGGCTTCTGGTTCAGTTCAAAATCGTTGAGAGATTGGCCTCTTTTCATGTGCTGTCTAACACTTCCAGTGTTCGCGCTT
5'RACE    (423)  CAGGCTTCTGGTTCAGT
5'RACEB   (325)
Consensus (482)  CAGGCTTCTGGTTCAGTTCAAAATCGTTGAGAGATTGGCCTCTTTTCATGTGCTGTCTAACACTTCCAGTGTTCGCGCTT 3'RACE      (1)
RT-PCR      (1)
amplicon1   (1)
amplicon2 (108)  GCTGCATATCTAGTTGAGAAATTGGCGTACCGGAAATATCTCTCTGAACCTATAGTCGTTTCCCTCCACATAATCATCTC
5'RACE    (438)
5'RACEB   (325)
Consensus (562)  GCTGCATATCTAGTTGAGAAATTGGCGTACCGGAAATATCTCTCTGAACCTATAGTCGTTTCCCTCCACATAATCATCTC
```

FIGURE 1A

```
3'RACE       (1)
RT-PCR       (1)
amplicon1    (1)
amplicon2  (188)  CGTGGTAGCAGTTGTGTACCCTGTTTCAGTGATTCTCAGCTGCGACTCTGCATTTGTATCTGGTGTGACGTTGATGCTTT
5'RACE     (438)
5'RACEB    (325)
Consensus  (642)  CGTGGTAGCAGTTGTGTACCCTGTTTCAGTGATTCTCAGCTGCGACTCTGCATTTGTATCTGGTGTGACGTTGATGCTTT 3'RACE       (1)
RT-PCR      (76)
amplicon1    (1)
amplicon2  (268)  TTGCTTGCATTGTGTGGTTAAAATTGGTCTCATATGCTCATACGAACTATGATATGAGAGCGGTTGCCAAGTCAGTTGAA
5'RACE     (438)
5'RACEB    (325)
Consensus  (722)  TTGCTTGCATTGTGTGGTTAAAATTGGTCTCATATGCTCATACGAACTATGATATGAGAGCGGTTGCCAAGTCAGTTGAA 3'RACE       (1)
RT-PCR     (156)
amplicon1    (1)
amplicon2  (348)  AAGGGAGAAGCACCTTCTGCTGCTTTGAATGTTGATTACTCTTATGACGTTAACTTCAAGAGCTTGGTGTATTTTATGAT
5'RACE     (438)
5'RACEB    (325)
Consensus  (802)  AAGGGAGAAGCACCTTCTGCTGCTTTGAATGTTGATTACTCTTATGACGTTAACTTCAAGAGCTTGGTGTATTTTATGAT 3'RACE       (1)
RT-PCR     (236)
amplicon1    (1)
amplicon2  (428)  TGCTCCAACACTGTGCTATCAGCCAAGCTATCCACGCACTCCATGTATCCGAAAGGGTTGGCTGGTTCATCAGTTCATCA
5'RACE     (438)
5'RACEB    (325)
Consensus  (882)  TGCTCCAACACTGTGCTATCAGCCAAGCTATCCACGCACTCCATGTATCCGAAAGGGTTGGCTGGTTCATCAGTTCATCA 3'RACE       (1)
RT-PCR     (316)       TTAGTAATATTTACAGGCTTGATGGGATTCATTATAGAGCAATATATCAATCCAATTATCCAGAACTCTCAGCATCCT
amplicon1    (1)
amplicon2  (508)  AGTTAGTAATATTTACAGGCTTGATGGGCTTCAT
5'RACE     (438)
5'RACEB    (325)
Consensus  (962)  AGTTAGTAATATTTACAGGCTTGATGGGATTCATTATAGAGCAATATATCAATCCAATTATCCAGAACTCTCAGCATCCT 3'RACE       (1)
RT-PCR     (396)  TTTAAAGGGAATCTATTATATGGAATTGAGAGGGTTTTGAAACTTTCGGTCCCAAACTTGTATGTGTGGCTGTGCATGTT
amplicon1    (1)
amplicon2  (540)
5'RACE     (438)
5'RACEB    (325)
Consensus (1042)  TTTAAAGGGAATCTATTATATGGAATTGAGAGGGTTTTGAAACTTTCGGTCCCAAACTTGTATGTGTGGCTGTGCATGTT 3'RACE       (1)                                                                            GCCATATCTATTTC
RT-PCR     (476)  CTACTGCTTCTTTCATCTATGGTTAAATATACTTGCAGAGCTCCTACGATTTGGTGATAGAGAATTCTACAAAGATTGGT
amplicon1    (1)                                                                                      TGGT
amplicon2  (540)
5'RACE     (438)
5'RACEB    (325)
Consensus (1122)  CTACTGCTTCTTTCATCTATGGTTAAATATACTTGCAGAGCTCCTACGATTTGGTGATAGAGAATTCTACAAAGATTGGT 3'RACE       (1)                                                                            GCCATATCTATTTC
RT-PCR     (556)  GGAATGCAAAAACTGTTGAAGAATACTGGAGAATGTGG
amplicon1   (66)  GGAATGCAAAAACTGTTGAAGAATACTGGAGAATGTGGAGCATGCCAGTTCATAAATGGATGGTTCGCCATATCTATTTC
amplicon2  (540)
5'RACE     (438)
5'RACEB    (325)
Consensus (1202)  GGAATGCAAAAACTGTTGAAGAATACTGGAGAATGTGGAGCATGCCAGTTCATAAATGGATGGTTCGCCATATCTATTTC
```

FIGURE 1B

```
     3'RACE    (74) CCATGTCTGCGGCACAACATTCCTAAGGGAGTAGCAATACTTATTGCCTTCTTTGTTTCTGCAGCATTTCATGAGTTGTG
     RT-PCR   (592)
   amplicon1  (146) CCATGTCTGCGGCACAACATTCCTAAGGGAGTAGCAATACTTATTGCCTTCTTTGTTTCTGCAGCATTTCATGAGTTGTG
   amplicon2  (540)
      5'RACE  (438)
     5'RACEB  (325)
  Consensus  (1282) CCATGTCTGCGGCACAACATTCCTAAGGGAGTAGCAATACTTATTGCCTTCTTTGTTTCTGCAGCATTTCATGAGTTGTG 3'RACE   (154) TATCGCAGTTCCTTGCCACATATTCAAGCTGTGGGCTTTTCTTGGGATTATGTTCCAGATTCCACTGGTGTGGATAACAA
     RT-PCR   (592)
   amplicon1  (226) TATCGCAGTTCC
   amplicon2  (540)
      5'RACE  (438)
     5'RACEB  (325)
  Consensus  (1362) TATCGCAGTTCCTTGCCACATATTCAAGCTGTGGGCTTTTCTTGGGATTATGTTCCAGATTCCACTGGTGTGGATAACAA 3'RACE   (234) ACGTTCTACAGCAGAAGTTCAAGAGCTCAATGGTGGGGAACATGATATTCTGGTCAATGTTCTGCATATTTGGTCAACCA
     RT-PCR   (592)
   amplicon1  (236)
   amplicon2  (540)
      5'RACE  (438)
     5'RACEB  (325)
  Consensus  (1442) ACGTTCTACAGCAGAAGTTCAAGAGCTCAATGGTGGGGAACATGATATTCTGGTCAATGTTCTGCATATTTGGTCAACCA 3'RACE   (314) ATGTGTGTGCTTCTATACTATCATGACTTGATGAACAGGAATGGGAAAGATGGAATCTGAAAAGGGAAACAAAAAACAAC
     RT-PCR   (592)
   amplicon1  (236)
   amplicon2  (540)
      5'RACE  (438)
     5'RACEB  (325)
  Consensus  (1522) ATGTGTGTGCTTCTATACTATCATGACTTGATGAACAGGAATGGGAAAGATGGAATCTGAAAAGGGAAACAAAAAACAAC 3'RACE   (394) TAATTCTTACTTGGTTCATTTCATTAGTGTTGTTGTTGCCTTGGAAATGGAGTGCATGCTTGGTTGCTTTAGAAAAGAGG
     RT-PCR   (592)
   amplicon1  (236)
   amplicon2  (540)
      5'RACE  (438)
     5'RACEB  (325)
  Consensus  (1602) TAATTCTTACTTGGTTCATTTCATTAGTGTTGTTGTTGCCTTGGAAATGGAGTGCATGCTTGGTTGCTTTAGAAAAGAGG 3'RACE   (474) AGAAAACCAAAGATACATTGAGGCGTTGTCTGCAATGTAATGGTAATGTTGGCGAGAATGTAAGAAAAGAAGCCATTTAT
     RT-PCR   (592)
   amplicon1  (236)
   amplicon2  (540)
      5'RACE  (438)
     5'RACEB  (325)
  Consensus  (1682) AGAAAACCAAAGATACATTGAGGCGTTGTCTGCAATGTAATGGTAATGTTGGCGAGAATGTAAGAAAAGAAGCCATTTAT 3'RACE   (554) TCGAAAAAAAAAAAAAAA
     RT-PCR   (592)
   amplicon1  (236)
   amplicon2  (540)
      5'RACE  (438)
     5'RACEB  (325)
  Consensus  (1762) TCGAAAAAAAAAAAAAAA
```

FIGURE 1C

```
1                                                                            80
CTTTCGGTGTGTTATCATCGTTCTTTCTGCGACTGCTTCCCCCCTCTCCTCTTCCAATGGCGGTGCTCGACACCCCTGAC
                                                                -M--A--V--L--D--T--P--D-

81                                                                          160
AATCACATAAACCCCTCTCCCTCCACCTCTGCTATTGACTCCTCCGATCTTAACGGTCTCTCCCTTCGACGTCGTTCAGT
-N--H--I--N--P--S--P--S--T--S--A--I--D--S--S--D--L--N--G--L--S--L--R--R--R--S--V 161                                                                         240
TGCCACTAACTCCGACCAAGGTACTTCTTCCACCGCTGTAGAATCACTCCACGCGGATCGGCCAGCCGATTCTGATGGGG
--A--T--N--S--D--Q--G--T--S--S--T--A--V--E--S--L--H--A--D--R--P--A--D--S--D--G--

241                                                                         320
CGAACCGCGAGGATAAGAAGATTGACAATCGGGACGGTCAAGTTGCGAGATCGGATATCAAATTCACTTACCGCCCTTCC
A--N--R--E--D--K--K--I--D--N--R--D--G--Q--V--A--R--S--D--I--K--F--T--Y--R--P--S-

321                                                                         400
GTGCCCGCTCACGTCAAGGTTAAAGAGAGTCCGCTTAGTTCCGGCGCCATTTTTAAGCAGAGCCATGCAGGCCTCTTCAA
-V--P--A--H--V--K--V--K--E--S--P--L--S--S--G--A--I--F--K--Q--S--H--A--G--L--F--N 401                                                                         480
TCTCTGTATTGTAGTCCTAGTTGCAGTCAACAGCAGGCTTATTATCGAGAATATCATGAAGTATGGTTGGTTAATTAGGA
--L--C--I--V--V--L--V--A--V--N--S--R--L--I--I--E--N--I--M--K--Y--G--W--L--I--R--

481                                                                         560
CAGGCTTCTGGTTCAGTTCAAAATCGTTGAGAGATTGGCCTCTTTTCATGTGCTGTCTAACACTTCCAGTGTTCGCGCTT
T--G--F--W--F--S--S--K--S--L--R--D--W--P--L--F--M--C--C--L--T--L--P--V--F--A--L-

561                                                                         640
GCTGCATATCTAGTTGAGAAATTGGCGTACCGGAAATATCTCTCTGAACCTATAGTCGTTTCCCTCCACATAATCATCTC
-A--A--Y--L--V--E--K--L--A--Y--R--K--Y--L--S--E--P--I--V--V--S--L--H--I--I--I--S 641                                                                         720
CGTGGTAGCAGTTGTGTACCCTGTTTCAGTGATTCTCAGCTGCGACTCTGCATTTGTATCTGGTGTGACGTTGATGCTTT
--V--V--A--V--V--Y--P--V--S--V--I--L--S--C--D--S--A--F--V--S--G--V--T--L--M--L--

721                                                                         800
TTGCTTGCATTGTGTGGTTAAAATTGGTCTCATATGCTCATACGAACTATGATATGAGAGCGGTTGCCAAGTCAGTTGAA
F--A--C--I--V--W--L--K--L--V--S--Y--A--H--T--N--Y--D--M--R--A--V--A--K--S--V--E-

801                                                                         880
AAGGGAGAAGCACCTTCTGCTGCTTTGAATGTTGATTACTCTTATGACGTTAACTTCAAGAGCTTGGTGTATTTTATGAT
-K--G--E--A--P--S--A--A--L--N--V--D--Y--S--Y--D--V--N--F--K--S--L--V--Y--F--M--I 881                                                                         960
TGCTCCAACACTGTGCTATCAGCCAAGCTATCCACGCACTCCATGTATCCGAAAGGGTTGGCTGGTTCATCAGTTCATCA
--A--P--T--L--C--Y--Q--P--S--Y--P--R--T--P--C--I--R--K--G--W--L--V--H--Q--F--I--

961                                                                        1040
AGTTAGTAATATTTACAGGCTTGATGGGATTCATTATAGAGCAATATATCAATCCAATTATCCAGAACTCTCAGCATCCT
K--L--V--I--F--T--G--L--M--G--F--I--I--E--Q--Y--I--N--P--I--Q--N--S--Q--H--P-

1041                                                                       1120
TTTAAAGGGAATCTATTATATGGAATTGAGAGGGTTTTGAAACTTTCGGTCCCAAACTTGTATGTGTGGCTGTGCATGTT
-F--K--G--N--L--L--Y--G--I--E--R--V--L--K--L--S--V--P--N--L--Y--V--W--L--C--M--F 1121                                                                       1200
CTACTGCTTCTTTCATCTATGGTTAAATATACTTGCAGAGCTCCTACGATTTGGTGATAGAGAATTCTACAAAGATTGGT
--Y--C--F--F--H--L--W--L--N--I--L--A--E--L--L--R--F--G--D--R--E--F--Y--K--D--W--
```

Fig 3. (1 /2)

```
1201                                                                          1280
GGAATGCAAAAACTGTTGAAGAATACTGGAGAATGTGGAGCATGCCAGTTCATAAATGGATGGTTCGCCATATCTATTTC
 W--N--A--K--T--V--E--E--Y--W--R--M--W--S--M--P--V--H--K--W--M--V--R--H--I--Y--F-

1281                                                                          1360
CCATGTCTGCGGCACAACATTCCTAAGGGAGTAGCAATACTTATTGCCTTCTTTGTTTCTGCAGCATTTCATGAGTTGTG
 -P--C--L--R--H--N--I--P--K--G--V--A--I--L--I--A--F--F--V--S--A--A--F--H--E--L--C 1361                                                                          1440
TATCGCAGTTCCTTGCCACATATTCAAGCTGTGGGCTTTTCTTGGGATTATGTTCCAGATTCCACTGGTGTGGATAACAA
 --I--A--V--P--C--H--I--F--K--L--W--A--F--L--G--I--M--F--Q--I--P--L--V--W--I--T--

1441                                                                          1520
ACGTTCTACAGCAGAAGTTCAAGAGCTCAATGGTGGGGAACATGATATTCTGGTCAATGTTCTGCATATTTGGTCAACCA
 N--V--L--Q--Q--K--F--K--S--S--M--V--G--N--M--I--F--W--S--M--F--C--I--F--G--Q--P-

1521                                                                          1600
ATGTGTGTGCTTCTATACTATCATGACTTGATGAACAGGAATGGGAAAGATGGAATCTGAAAAGGGAAACAAAAAACAAC
 -M--C--V--L--L--Y--Y--H--D--L--M--N--R--N--G--K--D--G--I--*-

1601                                                                          1680
TAATTCTTACTTGGTTCATTTCATTAGTGTTGTTGTTGCCTTGGAAATGGAGTGCATGCTTGGTTGCTTTAGAAAAGAGG 1681                                                                          1760
AGAAAACCAAAGATACATTGAGGCGTTGTCTGCAATGTAATGGTAATGTTGGCGAGAATGTAAGAAAAGAAGCCATTTAT 1761           1778
TCGAAAAAAAAAAAAAAA
```

```
                                                                                             549
AAD45536 Brassica napus     (438) CRLFNLWAFMGIMFVGVPLVFITNELQEREG-SMVGNMIFGSASCIFGQPMCGLLYYHDLMNRKGSMS---
AAY40784 Brassica juncea    (438) CRLFNLWAFMGIMFQVPLVFITNELQEREG-SMVGNMIFWFSFCIFGQPMCVLLYYHDLMNRKGSMS---
AAY40785 Brassica juncea    (438) CRLFNLWAFIGIMFQVPLVFITNYLQEREG-SMVGNMIFWFSFCIFGQPMCVLLYYHDLMNRKGSMS---
NP_179535 Arabidopsis thaliana (455) CRLFKLWAFIGIMFQVPLVFITNYLQEREG-STVGNMIFWFIFCIFGQPMCVLLYYHDLMNRKGSMS---
AAM03340 Tropaeolum majus   (454) CHVFKLWAFIGIMFQVPLVFLIINYLQNKFSNSMVGNMIFWFIFCILGQPMCVLLYYHDLINLKEK---
AAF19345 Nicotiana tabacum  (466) CRLFKWWAFMGIMFQVPIVIETHELQNKFQSSMVGNMIFWCFFCILGQPMCVLLYYHDLMNRKSSAR--
AAW47581 Oryza sativa       (472) CRILKFWAFIGIMLQIPLVITAYLKSKEDIMVGNMIFWFFFCIYGQPMCVLLYYHDLVMNRIEKAR---
AAG23696 Perilla frutescens (468) CQIFKFWAFSGIMLQVPIVTNYLQEKEGIKNSMVGNMIFWCFFCIFGQPMCVLLYYHDLMNRKASAR--
AAS01606 Olea europaea      (466) CHIFKFWAFIGIMFQVPIVPIVTNYLQDKFQNSMVGNMIFWCFFSILGQPMCILLYYHDLMNRKASAK--
AAS78662 Glycine max        (432) CHIFKLWAFIGIMFQVPIVPIVTNYLQNKERNSMVGNMIFWFIFSILGQPMCVLLYYHDLMNRKGKED--
BAE93460 Glycine max        (432) CHIFKLWAFIGIMFQVPIVPIVFITNYLQNKFRNSMVGNMIFWIFSILGHPMCVLLYYHDLMNRKGKED--
BAE93461 Glycine max        (438) CHIFKLWAFIGIMFQVPLVPIVLIINYLQNKFRNSMVGNMIFWFIFSILGQPMCVLLYYHDLMNRKGKED--
AAW51456 Lotus japonicus    (443) CHIFKLWAFIGIMFQVPLVPIPIVVITNYFQRKERSSMVGNMIFWFFFCILGQPMAVLLYYHDLMNRKSKEDQS
AAR11479 Ricinus communis   (457) CHMFKLWAFIGIMFQIPLVPIVGITNYLQNKERSSMVGNMIFWFIFCILGQPMCVLLYYHDLMNRSKEDQS
ABB84383 Jatropha curcas    (453) CHMFKLWAFIGIMFQIPIVPIVGITNYLQNKERSSMVGNMIFWFIFCILGQPMCLLLYYHDLMNRDGN---
ABC94471 Vernicia fordii    (458) CHIFKLWAFIGIMFQIPLVPIVLITSYLQNKERSSMVGNMIFWSFCILGQPMCLLLYYHDLMNRKGTTESR
AAV31083 Euonymus alatus    (441) CHIFKLWAFIGIMFQVPLVPIVFINYLQEREG-SMVGNMIFWFTFCIFGQPMCVLLYYHDLMNRKGKME--
AAF64065 Brassica napus     (436) CRLFKLWAFIGIMFQVPIVPIVWINVLQQKFKSSMVGNMIFWSMFCIFGQPMCVLLYYHDLMNRKGKMS--
LuDGAT1                     (440) CHIFKLWAFIGIMFQIPIVPIVWIITNYLQ KFR SMVGNMIFWF FCILGQPMCVLLYYHDLMNRNGKDGI-
Consensus                   (481) CHIFKLWAFIGIMFQIPIVPIV ITNYLQ KFR SMVGNMIFWF FCILGQPMCVLLYYHDLMNRKG M
```

Fig. 4D

SEQUENCE LISTING

```
<160> NUMBER OF SEQ ID NOS: 33

<210> SEQ ID NO 1
<211> LENGTH: 1778
<212> TYPE: DNA
<213> ORGANISM: Linum usitatissimum
<220> FEATURE:
<221> NAME/KEY: CDS
<222> LOCATION: (57)..(1580)
<223> OTHER INFORMATION: LuDGAT1

<400> SEQUENCE: 1
ctttcggtgt gttatcatcg ttctttctgc gactgcttcc cccctctcct cttcca atg      59
                                                                 Met
                                                                  1 gcg gtg ctc gac acc cct gac aat cac ata aac ccc tct ccc tcc acc       107
Ala Val Leu Asp Thr Pro Asp Asn His Ile Asn Pro Ser Pro Ser Thr
         5                  10                  15 tct gct att gac tcc tcc gat ctt aac ggt ctc tcc ctt cga cgt cgt       155
Ser Ala Ile Asp Ser Ser Asp Leu Asn Gly Leu Ser Leu Arg Arg Arg
             20                  25                  30 tca gtt gcc act aac tcc gac caa ggt act tct tcc acc gct gta gaa       203
Ser Val Ala Thr Asn Ser Asp Gln Gly Thr Ser Ser Thr Ala Val Glu
         35                  40                  45 tca ctc cac gcg gat cgg cca gcc gat tct gat ggg gcg aac cgc gag       251
Ser Leu His Ala Asp Arg Pro Ala Asp Ser Asp Gly Ala Asn Arg Glu
 50                  55                  60                  65 gat aag aag att gac aat cgg gac ggt caa gtt gcg aga tcg gat atc       299
Asp Lys Lys Ile Asp Asn Arg Asp Gly Gln Val Ala Arg Ser Asp Ile
                 70                  75                  80 aaa ttc act tac cgc cct tcc gtg ccc gct cac gtc aag gtt aaa gag       347
Lys Phe Thr Tyr Arg Pro Ser Val Pro Ala His Val Lys Val Lys Glu
             85                  90                  95 agt ccg ctt agt tcc ggc gcc att ttt aag cag agc cat gca ggc ctc       395
Ser Pro Leu Ser Ser Gly Ala Ile Phe Lys Gln Ser His Ala Gly Leu
        100                 105                 110 ttc aat ctc tgt att gta gtc cta gtt gca gtc aac agc agg ctt att       443
Phe Asn Leu Cys Ile Val Val Leu Val Ala Val Asn Ser Arg Leu Ile
    115                 120                 125 atc gag aat atc atg aag tat ggt tgg tta att agg aca ggc ttc tgg       491
Ile Glu Asn Ile Met Lys Tyr Gly Trp Leu Ile Arg Thr Gly Phe Trp
130                 135                 140                 145 ttc agt tca aaa tcg ttg aga gat tgg cct ctt ttc atg tgc tgt cta       539
Phe Ser Ser Lys Ser Leu Arg Asp Trp Pro Leu Phe Met Cys Cys Leu
                150                 155                 160 aca ctt cca gtg ttc gcg ctt gct gca tat cta gtt gag aaa ttg gcg       587
Thr Leu Pro Val Phe Ala Leu Ala Ala Tyr Leu Val Glu Lys Leu Ala
            165                 170                 175 tac cgg aaa tat ctc tct gaa cct ata gtc gtt tcc ctc cac ata atc       635
Tyr Arg Lys Tyr Leu Ser Glu Pro Ile Val Val Ser Leu His Ile Ile
        180                 185                 190 atc tcc gtg gta gca gtt gtg tac cct gtt tca gtg att ctc agc tgc       683
Ile Ser Val Val Ala Val Val Tyr Pro Val Ser Val Ile Leu Ser Cys
    195                 200                 205 gac tct gca ttt gta tct ggt gtg acg ttg atg ctt ttt gct tgc att       731
Asp Ser Ala Phe Val Ser Gly Val Thr Leu Met Leu Phe Ala Cys Ile
210                 215                 220                 225 gtg tgg tta aaa ttg gtc tca tat gct cat acg aac tat gat atg aga       779
Val Trp Leu Lys Leu Val Ser Tyr Ala His Thr Asn Tyr Asp Met Arg
                230                 235                 240
```

```
gcg gtt gcc aag tca gtt gaa aag gga gaa gca cct tct gct gct ttg      827
Ala Val Ala Lys Ser Val Glu Lys Gly Glu Ala Pro Ser Ala Ala Leu
        245                 250                 255 aat gtt gat tac tct tat gac gtt aac ttc aag agc ttg gtg tat ttt      875
Asn Val Asp Tyr Ser Tyr Asp Val Asn Phe Lys Ser Leu Val Tyr Phe
            260                 265                 270 atg att gct cca aca ctg tgc tat cag cca agc tat cca cgc act cca      923
Met Ile Ala Pro Thr Leu Cys Tyr Gln Pro Ser Tyr Pro Arg Thr Pro
275                 280                 285 tgt atc cga aag ggt tgg ctg gtt cat cag ttc atc aag tta gta ata      971
Cys Ile Arg Lys Gly Trp Leu Val His Gln Phe Ile Lys Leu Val Ile
290                 295                 300                 305 ttt aca ggc ttg atg gga ttc att ata gag caa tat atc aat cca att     1019
Phe Thr Gly Leu Met Gly Phe Ile Ile Glu Gln Tyr Ile Asn Pro Ile
                310                 315                 320 atc cag aac tct cag cat cct ttt aaa ggg aat cta tta tat gga att     1067
Ile Gln Asn Ser Gln His Pro Phe Lys Gly Asn Leu Leu Tyr Gly Ile
                325                 330                 335 gag agg gtt ttg aaa ctt tcg gtc cca aac ttg tat gtg tgg ctg tgc     1115
Glu Arg Val Leu Lys Leu Ser Val Pro Asn Leu Tyr Val Trp Leu Cys
            340                 345                 350 atg ttc tac tgc ttc ttt cat cta tgg tta aat ata ctt gca gag ctc     1163
Met Phe Tyr Cys Phe Phe His Leu Trp Leu Asn Ile Leu Ala Glu Leu
355                 360                 365 cta cga ttt ggt gat aga gaa ttc tac aaa gat tgg tgg aat gca aaa     1211
Leu Arg Phe Gly Asp Arg Glu Phe Tyr Lys Asp Trp Trp Asn Ala Lys
370                 375                 380                 385 act gtt gaa gaa tac tgg aga atg tgg agc atg cca gtt cat aaa tgg     1259
Thr Val Glu Glu Tyr Trp Arg Met Trp Ser Met Pro Val His Lys Trp
                390                 395                 400 atg gtt cgc cat atc tat ttc cca tgt ctg cgg cac aac att cct aag     1307
Met Val Arg His Ile Tyr Phe Pro Cys Leu Arg His Asn Ile Pro Lys
                405                 410                 415 gga gta gca ata ctt att gcc ttc ttt gtt tct gca gca ttt cat gag     1355
Gly Val Ala Ile Leu Ile Ala Phe Phe Val Ser Ala Ala Phe His Glu
            420                 425                 430 ttg tgt atc gca gtt cct tgc cac ata ttc aag ctg tgg gct ttt ctt     1403
Leu Cys Ile Ala Val Pro Cys His Ile Phe Lys Leu Trp Ala Phe Leu
435                 440                 445 ggg att atg ttc cag att cca ctg gtg tgg ata aca aac gtt cta cag     1451
Gly Ile Met Phe Gln Ile Pro Leu Val Trp Ile Thr Asn Val Leu Gln
450                 455                 460                 465 cag aag ttc aag agc tca atg gtg ggg aac atg ata ttc tgg tca atg     1499
Gln Lys Phe Lys Ser Ser Met Val Gly Asn Met Ile Phe Trp Ser Met
                470                 475                 480 ttc tgc ata ttt ggt caa cca atg tgt gtg ctt cta tac tat cat gac     1547
Phe Cys Ile Phe Gly Gln Pro Met Cys Val Leu Leu Tyr Tyr His Asp
                485                 490                 495 ttg atg aac agg aat ggg aaa gat gga atc tga aaagggaaac aaaaaacaac   1600
Leu Met Asn Arg Asn Gly Lys Asp Gly Ile
            500                 505 taattcttac ttggttcatt tcattagtgt tgttgttgcc ttggaaatgg agtgcatgct   1660
tggttgcttt agaaagagg agaaaaccaa agatacattg aggcgttgtc tgcaatgtaa    1720
tggtaatgtt ggcgagaatg taagaaaaga agccatttat tcgaaaaaaa aaaaaaaa    1778

<210> SEQ ID NO 2
<211> LENGTH: 507
<212> TYPE: PRT
<213> ORGANISM: Linum usitatissimum
```

<400> SEQUENCE: 2

```
Met Ala Val Leu Asp Thr Pro Asp Asn His Ile Asn Pro Ser Pro Ser
1               5                   10                  15

Thr Ser Ala Ile Asp Ser Ser Asp Leu Asn Gly Leu Ser Leu Arg Arg
            20                  25                  30

Arg Ser Val Ala Thr Asn Ser Asp Gln Gly Thr Ser Ser Thr Ala Val
        35                  40                  45

Glu Ser Leu His Ala Asp Arg Pro Ala Asp Ser Asp Gly Ala Asn Arg
    50                  55                  60

Glu Asp Lys Lys Ile Asp Asn Arg Asp Gly Gln Val Ala Arg Ser Asp
65                  70                  75                  80

Ile Lys Phe Thr Tyr Arg Pro Ser Val Pro Ala His Val Lys Val Lys
                85                  90                  95

Glu Ser Pro Leu Ser Ser Gly Ala Ile Phe Lys Gln Ser His Ala Gly
            100                 105                 110

Leu Phe Asn Leu Cys Ile Val Val Leu Val Ala Val Asn Ser Arg Leu
        115                 120                 125

Ile Ile Glu Asn Ile Met Lys Tyr Gly Trp Leu Ile Arg Thr Gly Phe
    130                 135                 140

Trp Phe Ser Ser Lys Ser Leu Arg Asp Trp Pro Leu Phe Met Cys Cys
145                 150                 155                 160

Leu Thr Leu Pro Val Phe Ala Leu Ala Ala Tyr Leu Val Glu Lys Leu
                165                 170                 175

Ala Tyr Arg Lys Tyr Leu Ser Glu Pro Ile Val Val Ser Leu His Ile
            180                 185                 190

Ile Ile Ser Val Val Ala Val Val Tyr Pro Val Ser Val Ile Leu Ser
        195                 200                 205

Cys Asp Ser Ala Phe Val Ser Gly Val Thr Leu Met Leu Phe Ala Cys
210                 215                 220

Ile Val Trp Leu Lys Leu Val Ser Tyr Ala His Thr Asn Tyr Asp Met
225                 230                 235                 240

Arg Ala Val Ala Lys Ser Val Glu Lys Gly Glu Ala Pro Ser Ala Ala
                245                 250                 255

Leu Asn Val Asp Tyr Ser Tyr Asp Val Asn Phe Lys Ser Leu Val Tyr
            260                 265                 270

Phe Met Ile Ala Pro Thr Leu Cys Tyr Gln Pro Ser Tyr Pro Arg Thr
        275                 280                 285

Pro Cys Ile Arg Lys Gly Trp Leu Val His Gln Phe Ile Lys Leu Val
    290                 295                 300

Ile Phe Thr Gly Leu Met Gly Phe Ile Ile Glu Gln Tyr Ile Asn Pro
305                 310                 315                 320

Ile Ile Gln Asn Ser Gln His Pro Phe Lys Gly Asn Leu Leu Tyr Gly
                325                 330                 335

Ile Glu Arg Val Leu Lys Leu Ser Val Pro Asn Leu Tyr Val Trp Leu
            340                 345                 350

Cys Met Phe Tyr Cys Phe Phe His Leu Trp Leu Asn Ile Leu Ala Glu
        355                 360                 365

Leu Leu Arg Phe Gly Asp Arg Glu Phe Tyr Lys Asp Trp Trp Asn Ala
    370                 375                 380

Lys Thr Val Glu Glu Tyr Trp Arg Met Trp Ser Met Pro Val His Lys
385                 390                 395                 400

Trp Met Val Arg His Ile Tyr Phe Pro Cys Leu Arg Ser Lys Ile Pro
                405                 410                 415
```

```
Lys Gly Val Ala Ile Leu Ile Ala Phe Phe Val Ser Ala Ala Phe His
            420                 425                 430

Glu Leu Cys Ile Ala Val Pro Cys His Ile Phe Lys Leu Trp Ala Phe
        435                 440                 445

Leu Gly Ile Met Phe Gln Ile Pro Leu Val Trp Ile Thr Asn Val Leu
    450                 455                 460

Gln Gln Lys Phe Lys Ser Ser Met Val Gly Asn Met Ile Phe Trp Ser
465                 470                 475                 480

Met Phe Cys Ile Phe Gly Gln Pro Met Cys Val Leu Leu Tyr Tyr His
                485                 490                 495

Asp Leu Met Asn Arg Asn Gly Lys Asp Gly Ile
        500                 505
```

<210> SEQ ID NO 3
<211> LENGTH: 1029
<212> TYPE: DNA
<213> ORGANISM: Linum usitatissimum
<220> FEATURE:
<221> NAME/KEY: CDS
<222> LOCATION: (1)..(1029)
<223> OTHER INFORMATION: LuDGAT2B

<400> SEQUENCE: 3

```
atg ggc cag aaa gta gag gag gaa aac cgg ctc gcc gga gga act gct        48
Met Gly Gln Lys Val Glu Glu Glu Asn Arg Leu Ala Gly Gly Thr Ala
1               5                   10                  15 tct aat agg tgg cag gag aat gta aac ggt aat agc atc aac ggc ggc        96
Ser Asn Arg Trp Gln Glu Asn Val Asn Gly Asn Ser Ile Asn Gly Gly
            20                  25                  30 gga gta gct acg att ttg aga tcc agt gat gtc gtc tct gga agc aaa       144
Gly Val Ala Thr Ile Leu Arg Ser Ser Asp Val Val Ser Gly Ser Lys
        35                  40                  45 ttg aag tct tta ttg tcg ctt ggg ata tgg ctg ggg gct atc cat ttc       192
Leu Lys Ser Leu Leu Ser Leu Gly Ile Trp Leu Gly Ala Ile His Phe
    50                  55                  60 aac gtc gcc tta ggt gtt gta tcc ttc gtc ttc ctc cct ttc tcc tat       240
Asn Val Ala Leu Gly Val Val Ser Phe Val Phe Leu Pro Phe Ser Tyr
65                  70                  75                  80 ttc ctg atg cta ttg gga ttt ctt ttg atg ttg atg ttc gtc cca atc       288
Phe Leu Met Leu Leu Gly Phe Leu Leu Met Leu Met Phe Val Pro Ile
                85                  90                  95 aac gat tcc agc tac ttg ggc cgc cga ttc tgc aga tac gtt tgc aga       336
Asn Asp Ser Ser Tyr Leu Gly Arg Arg Phe Cys Arg Tyr Val Cys Arg
            100                 105                 110 cat gcg tgt agt tac ttt ccg atc act ctt cac gtc gag gat atg aac       384
His Ala Cys Ser Tyr Phe Pro Ile Thr Leu His Val Glu Asp Met Asn
        115                 120                 125 gcc ttc cgt tct gat cgt tct tac gtt ttc ggg tat gag ccg cat tct       432
Ala Phe Arg Ser Asp Arg Ser Tyr Val Phe Gly Tyr Glu Pro His Ser
    130                 135                 140 gtt ctt ccc att ggc gtt gtt gct cta tcg gat cat gtg ggt ttt cta       480
Val Leu Pro Ile Gly Val Val Ala Leu Ser Asp His Val Gly Phe Leu
145                 150                 155                 160 cct cta ccg aaa att aaa gtt ctt gct ggc aca gct gtg ttc tac acc       528
Pro Leu Pro Lys Ile Lys Val Leu Ala Gly Thr Ala Val Phe Tyr Thr
                165                 170                 175 cct ttc ctt aga cat ata tgg acg tgg tgt ggt ctt gcc ccg gca acc       576
Pro Phe Leu Arg His Ile Trp Thr Trp Cys Gly Leu Ala Pro Ala Thr
            180                 185                 190 aag aag aat ttt acg tct ctc ttg gca tcc ggt tat agt tgc att gtg       624
Lys Lys Asn Phe Thr Ser Leu Leu Ala Ser Gly Tyr Ser Cys Ile Val
```

-continued

```
                195                 200                 205
gtt cct ggt ggc gtt caa gaa gca ttt cac atg gaa cat gga gca gag      672
Val Pro Gly Gly Val Gln Glu Ala Phe His Met Glu His Gly Ala Glu
    210                 215                 220 gtc gct ttc ctg aac aag cga aaa gga ttc gtt cgg tta gcc ata gag      720
Val Ala Phe Leu Asn Lys Arg Lys Gly Phe Val Arg Leu Ala Ile Glu
225                 230                 235                 240 atg ggt agc ccc ttg gtt cca gtt ttc tcc ttc ggt cag tca gat gtg      768
Met Gly Ser Pro Leu Val Pro Val Phe Ser Phe Gly Gln Ser Asp Val
                245                 250                 255 tac aag tgg tgg aaa cct agg gga aag tgg ttc ttg gca ttt gcg aga      816
Tyr Lys Trp Trp Lys Pro Arg Gly Lys Trp Phe Leu Ala Phe Ala Arg
            260                 265                 270 gct ata agg ttc acc cct att atc ttt tgg ggt ata ctc gga act cca      864
Ala Ile Arg Phe Thr Pro Ile Ile Phe Trp Gly Ile Leu Gly Thr Pro
        275                 280                 285 ttg cca ttc cag caa ccg atg cat gtt gtg att ggc cga ccc atc gaa      912
Leu Pro Phe Gln Gln Pro Met His Val Val Ile Gly Arg Pro Ile Glu
    290                 295                 300 ttt aag aaa aac gca cag cct agc atg gaa gag gtg gct gaa gtt cat      960
Phe Lys Lys Asn Ala Gln Pro Ser Met Glu Glu Val Ala Glu Val His
305                 310                 315                 320 ggg aag ttt gtt gca gca ctg aaa gac ctc ttt gat agg cac aaa gtg     1008
Gly Lys Phe Val Ala Ala Leu Lys Asp Leu Phe Asp Arg His Lys Val
                325                 330                 335 gag gct ggt tgt gct gat ctt                                         1029
Glu Ala Gly Cys Ala Asp Leu
            340
```

<210> SEQ ID NO 4
<211> LENGTH: 343
<212> TYPE: PRT
<213> ORGANISM: Linum usitatissimum

<400> SEQUENCE: 4

```
Met Gly Gln Lys Val Glu Glu Asn Arg Leu Ala Gly Gly Thr Ala
1               5                   10                  15

Ser Asn Arg Trp Gln Glu Asn Val Asn Gly Asn Ser Ile Asn Gly Gly
            20                  25                  30

Gly Val Ala Thr Ile Leu Arg Ser Ser Asp Val Ser Gly Ser Lys
        35                  40                  45

Leu Lys Ser Leu Leu Ser Leu Gly Ile Trp Leu Gly Ala Ile His Phe
    50                  55                  60

Asn Val Ala Leu Gly Val Val Ser Phe Val Phe Leu Pro Phe Ser Tyr
65                  70                  75                  80

Phe Leu Met Leu Leu Gly Phe Leu Leu Met Leu Met Phe Val Pro Ile
                85                  90                  95

Asn Asp Ser Ser Tyr Leu Gly Arg Arg Phe Cys Arg Tyr Val Cys Arg
            100                 105                 110

His Ala Cys Ser Tyr Phe Pro Ile Thr Leu His Val Glu Asp Met Asn
        115                 120                 125

Ala Phe Arg Ser Asp Arg Ser Tyr Val Phe Gly Tyr Glu Pro His Ser
    130                 135                 140

Val Leu Pro Ile Gly Val Val Ala Leu Ser Asp His Val Gly Phe Leu
145                 150                 155                 160

Pro Leu Pro Lys Ile Lys Val Leu Ala Gly Thr Ala Val Phe Tyr Thr
                165                 170                 175

Pro Phe Leu Arg His Ile Trp Thr Trp Cys Gly Leu Ala Pro Ala Thr
```

```
                      180              185              190
Lys Lys Asn Phe Thr Ser Leu Leu Ala Ser Gly Tyr Ser Cys Ile Val
        195                 200             205

Val Pro Gly Val Gln Glu Ala Phe His Met Glu His Gly Ala Glu
    210                 215                 220

Val Ala Phe Leu Asn Lys Arg Lys Gly Phe Val Arg Leu Ala Ile Glu
225                 230                 235                 240

Met Gly Ser Pro Leu Val Pro Val Phe Ser Phe Gly Gln Ser Asp Val
                    245                 250                 255

Tyr Lys Trp Trp Lys Pro Arg Gly Lys Trp Phe Leu Ala Phe Ala Arg
            260                 265                 270

Ala Ile Arg Phe Thr Pro Ile Ile Phe Trp Gly Ile Leu Gly Thr Pro
            275                 280                 285

Leu Pro Phe Gln Gln Pro Met His Val Val Ile Gly Arg Pro Ile Glu
            290                 295                 300

Phe Lys Lys Asn Ala Gln Pro Ser Met Glu Glu Val Ala Glu Val His
305                 310                 315                 320

Gly Lys Phe Val Ala Ala Leu Lys Asp Leu Phe Asp Arg His Lys Val
                325                 330                 335

Glu Ala Gly Cys Ala Asp Leu
            340

<210> SEQ ID NO 5
<211> LENGTH: 1047
<212> TYPE: DNA
<213> ORGANISM: Linum usitatissimum
<220> FEATURE:
<221> NAME/KEY: CDS
<222> LOCATION: (1)..(1047)
<223> OTHER INFORMATION: LuDGT2B

<400> SEQUENCE: 5 atg ggc cag aaa gta gag gag gaa gac cgg ctc gcc gga gga act gct      48
Met Gly Gln Lys Val Glu Glu Glu Asp Arg Leu Ala Gly Gly Thr Ala
1               5                   10                  15 tct aat agc tgg cag gag aac gta aac ggt aat agc att aac ggt ggc      96
Ser Asn Ser Trp Gln Glu Asn Val Asn Gly Asn Ser Ile Asn Gly Gly
                20                  25                  30 ggc ggc ggt gga gga gga gga gtt gct acg att ttg aga tcc act gat     144
Gly Gly Gly Gly Gly Gly Gly Val Ala Thr Ile Leu Arg Ser Thr Asp
            35                  40                  45 gtc gtc tct aga agc aaa ttg aag tct tta ttg tcg ctt ggg ata tgg     192
Val Val Ser Arg Ser Lys Leu Lys Ser Leu Leu Ser Leu Gly Ile Trp
        50                  55                  60 ctg ggg gct atc cat ttc aac gtc gcc tta gtt gtt gta tcc ttc gtc     240
Leu Gly Ala Ile His Phe Asn Val Ala Leu Val Val Val Ser Phe Val
65                  70                  75                  80 ttc ctc cct ttc tcc tat ttc ctg atg cta ttg gga ttt ctt ttg atg     288
Phe Leu Pro Phe Ser Tyr Phe Leu Met Leu Leu Gly Phe Leu Leu Met
                    85                  90                  95 ttg gtg ttc att cca atc aac gat tcc agc tac ttg ggc cgc cga ttc     336
Leu Val Phe Ile Pro Ile Asn Asp Ser Ser Tyr Leu Gly Arg Arg Phe
                100                 105                 110 tgc aga tac gtt tgc aga cat gcg tgt agt tac ttt ccg atc act ctt     384
Cys Arg Tyr Val Cys Arg His Ala Cys Ser Tyr Phe Pro Ile Thr Leu
            115                 120                 125 cat gtc gag gat atc aac gcc ttc cgt tct gat cgt tct tac gtt ttc     432
His Val Glu Asp Ile Asn Ala Phe Arg Ser Asp Arg Ser Tyr Val Phe
        130                 135                 140
```

```
ggg tac gag ccg cat tct gtt ctt ccc att ggc gtt gtt gtt cta tcg     480
Gly Tyr Glu Pro His Ser Val Leu Pro Ile Gly Val Val Val Leu Ser
145                 150                 155                 160 gat cat gtg ggt ttt ctg cct tta ccg aag ata aaa gtt ctt gct agc     528
Asp His Val Gly Phe Leu Pro Leu Pro Lys Ile Lys Val Leu Ala Ser
                165                 170                 175 aca gct gtg ttc tat acc cct ttc ctt aga cat ata tgg acg tgg tgt     576
Thr Ala Val Phe Tyr Thr Pro Phe Leu Arg His Ile Trp Thr Trp Cys
            180                 185                 190 ggt ctt gcc ccg gca acc aag aag aat ttc acg tct ctc ttg gca tcc     624
Gly Leu Ala Pro Ala Thr Lys Lys Asn Phe Thr Ser Leu Leu Ala Ser
        195                 200                 205 ggt tat agt tgc att gtg gtt ccc ggt ggc gtt caa gaa gca ttt cac     672
Gly Tyr Ser Cys Ile Val Val Pro Gly Gly Val Gln Glu Ala Phe His
    210                 215                 220 atg gaa cat gga gta gag gtc gct ttc ctg aac aag cga aaa gga ttc     720
Met Glu His Gly Val Glu Val Ala Phe Leu Asn Lys Arg Lys Gly Phe
225                 230                 235                 240 gtt cgg tta gcc ata gag atg ggt agc ccc ttg gtt cct gtt ttc tcc     768
Val Arg Leu Ala Ile Glu Met Gly Ser Pro Leu Val Pro Val Phe Ser
                245                 250                 255 ttc ggt cag tcg gat gtg tac aag tgg tgg aaa cct agg gga aag tgg     816
Phe Gly Gln Ser Asp Val Tyr Lys Trp Trp Lys Pro Arg Gly Lys Trp
            260                 265                 270 ttc ttg gca ttt gcg aga gtg att agg ttc acc cct att atc ttt tgg     864
Phe Leu Ala Phe Ala Arg Val Ile Arg Phe Thr Pro Ile Ile Phe Trp
        275                 280                 285 ggt gta ctc gga act cca ttg cca ttc cgg caa cca atg cac gtt gtg     912
Gly Val Leu Gly Thr Pro Leu Pro Phe Arg Gln Pro Met His Val Val
    290                 295                 300 atc ggc cga ccc atc gaa ttt aag aaa aac gca cag cct acc atg gaa     960
Ile Gly Arg Pro Ile Glu Phe Lys Lys Asn Ala Gln Pro Thr Met Glu
305                 310                 315                 320 gag gtg gct gaa gtt cat ggg cag ttt gtt gca gca ctg aaa gac ctc    1008
Glu Val Ala Glu Val His Gly Gln Phe Val Ala Ala Leu Lys Asp Leu
                325                 330                 335 ttt gat agg cac aaa gtg gag gct ggc tgt gct gat ctt                1047
Phe Asp Arg His Lys Val Glu Ala Gly Cys Ala Asp Leu
            340                 345

<210> SEQ ID NO 6
<211> LENGTH: 349
<212> TYPE: PRT
<213> ORGANISM: Linum usitatissimum

<400> SEQUENCE: 6

Met Gly Gln Lys Val Glu Glu Asp Arg Leu Ala Gly Gly Thr Ala
1               5                   10                  15

Ser Asn Ser Trp Gln Glu Asn Val Asn Gly Asn Ser Ile Asn Gly Gly
            20                  25                  30

Gly Gly Gly Gly Gly Gly Val Ala Thr Ile Leu Arg Ser Thr Asp
        35                  40                  45

Val Val Ser Arg Ser Lys Leu Lys Ser Leu Leu Ser Leu Gly Ile Trp
    50                  55                  60

Leu Gly Ala Ile His Phe Asn Val Ala Leu Val Val Val Ser Phe Val
65                  70                  75                  80

Phe Leu Pro Phe Ser Tyr Phe Leu Met Leu Leu Gly Phe Leu Leu Met
                85                  90                  95

Leu Val Phe Ile Pro Ile Asn Asp Ser Ser Tyr Leu Gly Arg Arg Phe
            100                 105                 110
```

Cys Arg Tyr Val Cys Arg His Ala Cys Ser Tyr Phe Pro Ile Thr Leu
            115                 120                 125

His Val Glu Asp Ile Asn Ala Phe Arg Ser Asp Arg Ser Tyr Val Phe
        130                 135                 140

Gly Tyr Glu Pro His Ser Val Leu Pro Ile Gly Val Val Val Leu Ser
145                 150                 155                 160

Asp His Val Gly Phe Leu Pro Leu Pro Lys Ile Lys Val Leu Ala Ser
                165                 170                 175

Thr Ala Val Phe Tyr Thr Pro Phe Leu Arg His Ile Trp Thr Trp Cys
            180                 185                 190

Gly Leu Ala Pro Ala Thr Lys Lys Asn Phe Thr Ser Leu Leu Ala Ser
        195                 200                 205

Gly Tyr Ser Cys Ile Val Val Pro Gly Val Gln Glu Ala Phe His
        210                 215                 220

Met Glu His Gly Val Glu Val Ala Phe Leu Asn Lys Arg Lys Gly Phe
225                 230                 235                 240

Val Arg Leu Ala Ile Glu Met Gly Ser Pro Leu Val Pro Val Phe Ser
            245                 250                 255

Phe Gly Gln Ser Asp Val Tyr Lys Trp Trp Lys Pro Arg Gly Lys Trp
            260                 265                 270

Phe Leu Ala Phe Ala Arg Val Ile Arg Phe Thr Pro Ile Ile Phe Trp
        275                 280                 285

Gly Val Leu Gly Thr Pro Leu Pro Phe Arg Gln Pro Met His Val Val
        290                 295                 300

Ile Gly Arg Pro Ile Glu Phe Lys Lys Asn Ala Gln Pro Thr Met Glu
305                 310                 315                 320

Glu Val Ala Glu Val His Gly Gln Phe Val Ala Ala Leu Lys Asp Leu
                325                 330                 335

Phe Asp Arg His Lys Val Glu Ala Gly Cys Ala Asp Leu
            340                 345

<210> SEQ ID NO 7
<211> LENGTH: 39
<212> TYPE: DNA
<213> ORGANISM: Artificial sequence
<220> FEATURE:
<223> OTHER INFORMATION: chemically synthetized
<220> FEATURE:
<221> NAME/KEY: misc_feature
<222> LOCATION: (1)..(39)
<223> OTHER INFORMATION: oligodT adaptor
<220> FEATURE:
<221> NAME/KEY: misc_feature
<222> LOCATION: (39)..(39)
<223> OTHER INFORMATION: n is a, c, g, or t

<400> SEQUENCE: 7
ggccacgcgt cgactagtac tttttttttt ttttttttvn                          39

<210> SEQ ID NO 8
<211> LENGTH: 21
<212> TYPE: DNA
<213> ORGANISM: artificial sequence
<220> FEATURE:
<223> OTHER INFORMATION: chemically synthetized
<220> FEATURE:
<221> NAME/KEY: misc_feature
<222> LOCATION: (1)..(21)
<223> OTHER INFORMATION: oligonucleotide RS-007
<220> FEATURE:
<221> NAME/KEY: misc_feature
<222> LOCATION: (12)..(12)

```
<223> OTHER INFORMATION: n is a, c, g, or t

<400> SEQUENCE: 8
garttytayc angaytggtg g                                              21

<210> SEQ ID NO 9
<211> LENGTH: 23
<212> TYPE: DNA
<213> ORGANISM: artificial sequence
<220> FEATURE:
<221> NAME/KEY: misc_feature
<222> LOCATION: (1)..(23)
<223> OTHER INFORMATION: oligonucleotide RS-008
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t

<400> SEQUENCE: 9
ggnacngcna trcanarytc rtg                                            23

<210> SEQ ID NO 10
<211> LENGTH: 20
<212> TYPE: DNA
<213> ORGANISM: artificial sequence
<220> FEATURE:
<223> OTHER INFORMATION: chemically synthetized
<220> FEATURE:
<221> NAME/KEY: misc_feature
<222> LOCATION: (1)..(20)
<223> OTHER INFORMATION: oligonucleotide RS-009
<220> FEATURE:
<221> NAME/KEY: misc_feature
<222> LOCATION: (6)..(6)
<223> OTHER INFORMATION: n is a, c, g or t
<220> FEATURE:
<221> NAME/KEY: misc_feature
<222> LOCATION: (9)..(9)
<223> OTHER INFORMATION: n is a, c, g or t

<400> SEQUENCE: 10
garaanytna tgaartaygg                                                20

<210> SEQ ID NO 11
<211> LENGTH: 23
<212> TYPE: DNA
<213> ORGANISM: artificial sequence
<220> FEATURE:
<223> OTHER INFORMATION: chemically synthetized
<220> FEATURE:
<221> NAME/KEY: misc_feature
<222> LOCATION: (1)..(23)
<223> OTHER INFORMATION: oligonucleotide RS-010
<220> FEATURE:
<221> NAME/KEY: misc_feature
<222> LOCATION: (3)..(3)
<223> OTHER INFORMATION: n is a,c , g or t
<220> FEATURE:
<221> NAME/KEY: misc_feature
<222> LOCATION: (9)..(9)
<223> OTHER INFORMATION: n is a,c , g or t
<220> FEATURE:
```

```
<221> NAME/KEY: misc_feature
<222> LOCATION: (18)..(8)
<223> OTHER INFORMATION: n is a,c , g or t

<400> SEQUENCE: 11
tantgytcna tdatraancc cat                                              23

<210> SEQ ID NO 12
<211> LENGTH: 26
<212> TYPE: DNA
<213> ORGANISM: artificial sequence
<220> FEATURE:
<223> OTHER INFORMATION: chemically synthetized
<220> FEATURE:
<221> NAME/KEY: misc_feature
<222> LOCATION: (1)..(26)
<223> OTHER INFORMATION: oligonucleotide RS-027

<400> SEQUENCE: 12
gccatatcta tttcccatgt ctgcgg                                           26

<210> SEQ ID NO 13
<211> LENGTH: 20
<212> TYPE: DNA
<213> ORGANISM: artificial sequence
<220> FEATURE:
<223> OTHER INFORMATION: chemically synthetized
<220> FEATURE:
<221> NAME/KEY: misc_feature
<222> LOCATION: (1)..(20)
<223> OTHER INFORMATION: oligonucelotide adaptor

<400> SEQUENCE: 13
ggccacgcgt cgactagtac                                                  20

<210> SEQ ID NO 14
<211> LENGTH: 19
<212> TYPE: DNA
<213> ORGANISM: artificial sequence
<220> FEATURE:
<223> OTHER INFORMATION: chemically syntetized
<220> FEATURE:
<221> NAME/KEY: misc_feature
<222> LOCATION: (1)..(19)
<223> OTHER INFORMATION: oligonucletoide RS-039

<400> SEQUENCE: 14
cactggaagt gttagacag                                                   19

<210> SEQ ID NO 15
<211> LENGTH: 38
<212> TYPE: DNA
<213> ORGANISM: artificial sequence
<220> FEATURE:
<223> OTHER INFORMATION: chemically syntehtized
<220> FEATURE:
<221> NAME/KEY: misc_feature
<222> LOCATION: (1)..(38)
<223> OTHER INFORMATION: oligonucleotide oligo dG adaptor
<220> FEATURE:
<221> NAME/KEY: misc_feature
<222> LOCATION: (38)..(38)
<223> OTHER INFORMATION: n is a,c, g or t

<400> SEQUENCE: 15
ggccacgcgt cgactagtac gggggggggg gggggggn                              38

<210> SEQ ID NO 16
<211> LENGTH: 19
<212> TYPE: DNA
```

```
<213> ORGANISM: artificial sequence
<220> FEATURE:
<223> OTHER INFORMATION: chemically sytnetized
<220> FEATURE:
<221> NAME/KEY: misc_feature
<222> LOCATION: (1)..(19)
<223> OTHER INFORMATION: oligonucleotide RS-038

<400> SEQUENCE: 16
actgaaccag aagcctgtc                                               19

<210> SEQ ID NO 17
<211> LENGTH: 19
<212> TYPE: DNA
<213> ORGANISM: artificial sequence
<220> FEATURE:
<223> OTHER INFORMATION: chemically syntehtized
<220> FEATURE:
<221> NAME/KEY: misc_feature
<222> LOCATION: (1)..(19)
<223> OTHER INFORMATION: oligonucleotide  RS-057

<400> SEQUENCE: 17
cggaactaag cggactctc                                               19

<210> SEQ ID NO 18
<211> LENGTH: 19
<212> TYPE: DNA
<213> ORGANISM: artificial sequence
<220> FEATURE:
<223> OTHER INFORMATION: chemically synthetized
<220> FEATURE:
<221> NAME/KEY: misc_feature
<222> LOCATION: (1)..(19)
<223> OTHER INFORMATION: oligonucleotide  RS-056

<400> SEQUENCE: 18
ggcacggaag ggcggtaag                                               19

<210> SEQ ID NO 19
<211> LENGTH: 22
<212> TYPE: DNA
<213> ORGANISM: artificial sequence
<220> FEATURE:
<223> OTHER INFORMATION: chemically synthtetized
<220> FEATURE:
<221> NAME/KEY: misc_feature
<222> LOCATION: (1)..(22)
<223> OTHER INFORMATION: oligonucleotide RS-054

<400> SEQUENCE: 19
caagttagta atatttacag gc                                           22

<210> SEQ ID NO 20
<211> LENGTH: 22
<212> TYPE: DNA
<213> ORGANISM: artificial sequence
<220> FEATURE:
<223> OTHER INFORMATION: chemically synthetized
<220> FEATURE:
<221> NAME/KEY: misc_feature
<222> LOCATION: (1)..(22)
<223> OTHER INFORMATION: oligonucleotide RS-055

<400> SEQUENCE: 20
tccacattct ccagtattct tc                                           22

<210> SEQ ID NO 21
<211> LENGTH: 42
<212> TYPE: DNA
```

```
<213> ORGANISM: artificial sequence
<220> FEATURE:
<223> OTHER INFORMATION: chemically synthetized
<220> FEATURE:
<221> NAME/KEY: misc_feature
<222> LOCATION: (1)..(42)
<223> OTHER INFORMATION: oligonucleotide RS-100

<400> SEQUENCE: 21
attaggatcc gaccatgggc gtgctcgaca ctcctgacaa tc                          42

<210> SEQ ID NO 22
<211> LENGTH: 31
<212> TYPE: DNA
<213> ORGANISM: artificial sequence
<220> FEATURE:
<223> OTHER INFORMATION: chemically synthetized
<220> FEATURE:
<221> NAME/KEY: misc_feature
<222> LOCATION: (1)..(31)
<223> OTHER INFORMATION: oligonucleotide RS-101

<400> SEQUENCE: 22
tttaagcttg attccatctt tcccattcct g                                     31

<210> SEQ ID NO 23
<211> LENGTH: 8
<212> TYPE: PRT
<213> ORGANISM: Linum usitatissimum
<220> FEATURE:
<221> NAME/KEY: PEPTIDE
<222> LOCATION: (1)..(8)
<223> OTHER INFORMATION: LuDGAT1 residues from 253 to 259

<400> SEQUENCE: 23

Ala Pro Ser Ala Ala Leu Asn Val
1               5

<210> SEQ ID NO 24
<211> LENGTH: 7
<212> TYPE: PRT
<213> ORGANISM: Linum usitatissimum

<400> SEQUENCE: 24

Glu Ser Pro Leu Ser Ser Asp
1               5

<210> SEQ ID NO 25
<211> LENGTH: 4
<212> TYPE: PRT
<213> ORGANISM: Brassica
<220> FEATURE:
<221> NAME/KEY: PEPTIDE
<222> LOCATION: (1)..(4)
<223> OTHER INFORMATION: amino acid sequences in DGAT position 301-307

<400> SEQUENCE: 25

Leu Ala Tyr Phe
1

<210> SEQ ID NO 26
<211> LENGTH: 4
<212> TYPE: PRT
<213> ORGANISM: Linum usitatissimum
<220> FEATURE:
<221> NAME/KEY: PEPTIDE
<222> LOCATION: (1)..(4)
<223> OTHER INFORMATION: amino acid sequence in LuDGAT in positions
      311-314
<220> FEATURE:
```

<221> NAME/KEY: PEPTIDE
<222> LOCATION: (1)..(4)
<223> OTHER INFORMATION: amino acid sequence in LuDGAT in positions
      271-275

<400> SEQUENCE: 26

Leu Val Tyr Phe
1

<210> SEQ ID NO 27
<211> LENGTH: 7
<212> TYPE: PRT
<213> ORGANISM: Brassica napus
<220> FEATURE:
<221> NAME/KEY: PEPTIDE
<222> LOCATION: (1)..(7)
<223> OTHER INFORMATION: amino acid sequence of DGAT in positions
      234-241

<400> SEQUENCE: 27

Met Trp Asn Met Pro Val His
1               5

<210> SEQ ID NO 28
<211> LENGTH: 176
<212> TYPE: DNA
<213> ORGANISM: Linum usitatissimum
<220> FEATURE:
<221> NAME/KEY: misc_feature
<222> LOCATION: (1)..(176)
<223> OTHER INFORMATION: isolated nucleotide fragment amplicon 1

<400> SEQUENCE: 28
tggtggaatg caaaaactgt tgaagaatac tggagaatgt ggagcatgcc agttcataaa      60
tggatggttc gccatatcta tttcccatgt ctgcggcaca acattcctaa gggagtagca     120
atacttattg ccttctttgt ttctgcagca tttcatgagt tgtgtatcgc agttcc         176

<210> SEQ ID NO 29
<211> LENGTH: 539
<212> TYPE: DNA
<213> ORGANISM: linum usitatissimum
<220> FEATURE:
<221> NAME/KEY: misc_feature
<222> LOCATION: (1)..(539)
<223> OTHER INFORMATION: isolated polynucleotide frgment amplicon 2.

<400> SEQUENCE: 29
atgaagtatg gttggttaat taggacaggc ttctggttca gttcaaaatc gttgagattg      60
gcctcttttc atgtgctgtc taacacttcc agtgttcgcg cttgctgcat atctagttga     120
ggaaattggc gtaccggaaa tatctctctg aacctatagt cgtttccctc cacataatca     180
tctccgtggg tagcagttgt gtaccctgtt tcagtgattc tcagctgcga ctctgcattt     240
gtatctggtg tgacgttgat gcttttgct tgcattgtgt ggttaaaatt ggtctcatat      300
gctcatacga actatgatat gagagcggtt gccaagtcag ttgaaaaggg agaagcacct     360
tctgctgctt tgaatgttga ttactcttat gacgttaact tcaagagctt ggtgtatttt     420
atgattgctc caacactgtg ctatcagcca agctatccac gcactccatg tatccgaaag     480
ggttggctgg ttcatcagtt catcaagtta gtaatattta caggcttgat gggcttcat     539

<210> SEQ ID NO 30
<211> LENGTH: 275
<212> TYPE: DNA
<213> ORGANISM: Linum usitatissimum
<220> FEATURE:

```
<221> NAME/KEY: misc_feature
<222> LOCATION: (1)..(275)
<223> OTHER INFORMATION: isolated RT-PCR polynucleotide fragment

<400> SEQUENCE: 30
ttagtaatat ttacaggctt gatgggattc attatagagc aatatatcaa tccaattatc    60
cagaactctc agcatccttt taaagggaat ctattatatg gaattgagag ggttttgaaa   120
ctttcggtcc caaacttgta tgtgtggctg tgcatgttct actgcttctt tcatctatgg   180
taaatatact tgcagagctc ctacgatttg gtgatagaga attctacaaa gattggtgga   240
atgcaaaaac tgttgaagaa tactggagaa tgtgg                              275

<210> SEQ ID NO 31
<211> LENGTH: 438
<212> TYPE: DNA
<213> ORGANISM: Linum usitatissimum
<220> FEATURE:
<221> NAME/KEY: misc_feature
<222> LOCATION: (1)..(438)
<223> OTHER INFORMATION: isolated 5'RACE polynucleotide fragment

<400> SEQUENCE: 31
cggtgctcga caccccctgac aatcacataa accccctctcc ctccacctct gctattgact   60
```

```
cggtgctcga caccccctgac aatcacataa accccctctcc ctccacctct gctattgact   60
cctccgatct taacggtctc tcccttcgac gtcgttcagt tgccactaac tcccgaccaa   120
ggtacttctt ccaccgctgt agaatcactc cacgcggatc ggccagccga ttctgatggg   180
gcgaaccgcg aggataagaa gattgacaat cgggacggtc aagttgcgag atcggatatc   240
aaattcactt accgcccttc cgtgcccgct cacgtcaagg ttaaagagag tccgcttagt   300
tccggcgcca tttttaagca gagccatgca ggcctcttca atctctgtat tgtagtccta   360
gttgcagtca acagcaggct tattatcgag aatatcatga agtatggttg gttaattagg   420
acaggcttct ggttcagt                                                  438

<210> SEQ ID NO 32
<211> LENGTH: 327
<212> TYPE: DNA
<213> ORGANISM: Linum usitatissimum
<220> FEATURE:
<221> NAME/KEY: misc_feature
<222> LOCATION: (1)..(327)
<223> OTHER INFORMATION: isolated 5'RACEB polynucleotide fragment

<400> SEQUENCE: 32
ctttcggtgt gttatcatcg ttctttctgc gactgcttcc ccctctcct cttccaatgg     60 cggtgctcga caccccctgac aatcacataa accccctctcc ctccacctct gctattgact  120
ccctccgatc ttaacggtct ctcccttcga cgtcgttcag ttgccactaa ctccgaccaa   180
ggtacttctt ccaaccgctg tagaatcact ccacgcggat cggccagccg attctgatgg   240
ggcgaaccgc gaggataaga agattgacaa tcgggacggt caagttgcga gatcggatat   300
caaattcact taccgcccct tccgtgcc                                       327

<210> SEQ ID NO 33
<211> LENGTH: 511
<212> TYPE: DNA
<213> ORGANISM: Linum usitatissimum
<220> FEATURE:
<221> NAME/KEY: misc_feature
<222> LOCATION: (1)..(511)
<223> OTHER INFORMATION: isolated 3'RACE polynucleotide fragment

<400> SEQUENCE: 33
```

```
gccatatcta tttcccatgt ctgcggcaca acattcctaa gggagtagca atacttattg      60
ccttctttgt ttctgcagca tttcatgagt tgtgtatcga gttccttgcc acatattcaa     120
gctgtgggct tttcttggga ttatgttcca gattccactg gtgtggataa caaacgttct     180
acagcagaag ttcaagagct caatggtggg gaacatgata ttctggtcaa tgttctgcat     240
atttggtcaa ccaatgtgtg tgcttctata ctatcatgac ttgatgaaca ggaatgggaa     300
agatggaatc tgaaaaggga aacaaaaaac aactaattct tacttggttc atttcattag     360
tgttgttgtt gccttggaaa tggagtgcat gcttggttgt tttagaaaag aggagaaaac     420
caaagataca ttgaggcgtt gtctgcaatg taatggtaat gttggcgaga atgtaagaaa     480
agaagccatt tattcgaaaa aaaaaaaaaa a                                    511
```

DIACYLGLYCEROL ACYLTRANSFERASES FROM FLAX

PRIORITY

This application claims priority of U.S. provisional application No. 61/034,787 filed on Mar. 7, 2008

FIELD OF THE INVENTION

The present invention relates to isolated diacylglycerol acyltransferases and polynucleotide sequences encoding the DGAT enzymes; polynucleotide constructs, vectors and host cells incorporating the polynucleotide sequences; and methods of producing and using same.

BACKGROUND

Oils obtained from plant seeds are important sources of fatty acids for human consumption and for use as chemical feedstocks. These fatty acids include essential fatty acids, saturated fatty acids, monounsaturated fatty acids, and polyunsaturated fatty acids. In plant seed oils, fatty acids are stored predominantly as triacylglycerols (TAGs). TAGs represent the most efficient form of stored energy in eukaryotic cells.

TAG biosynthesis occurs mainly in the endoplasmic reticulum (ER) of the cell using acyl-CoA and sn-glycerol-3-phosphate as primary substrates. Biosynthesis of TAG is effected through a biochemical process generally known as the Kennedy pathway (Kennedy, 1961) which involves the sequential transfer of fatty acids from acyl-CoAs to the glycerol backbone (acyl-CoA-dependent acylation). The pathway starts with the acylation of sn-glycerol-3-phosphate to form lysophosphatidic acid through the action of sn-glycerol-3-phosphate acyltransferase. The second acylation is catalyzed by lysophosphatidic acid acyltransferase, leading to the formation of phosphatidic acid which is dephosphorylated by phosphatidate phosphatase1 to form sn-1,2-diacylglycerol. The final acylation is catalyzed by diacylglycerol acyltransferase (DGAT; EC 2.3.1.20) to form TAG. The DGAT enzyme catalyzes the transference of the acyl group from acyl-coenzymeA (acyl-CoA) donor to a sn-1,2-diacylglycerol, producing CoA and TAG. Previous research results suggest that the level of DGAT activity may have a substantial effect in the flow of carbon into seed oil (Ichihara and Noda, 1988; Perry and Harwood, 1993; Stobart et al., 1986; Settlage et al., 1998).

Two types of DGAT (DGAT1 and DGAT2) have been identified in animals and plants (Cases et al., 2001; Hobbs et al., 1999; Lardizabal et al., 2001; Kroon et al., 2006; Shockey et al., 2006). DGAT1 has been most studied and displays broad substrate specificity. DGAT1 null mutants in plants and animals have been shown to have substantially reduced levels of TAG (Routaboul et al., 1999; Smith et al., 2000). Furthermore, over-expression of DGAT1 in seeds of *Arabidopsis thaliana* results in increased seed weight and oil content (Jako et al., 2001). These results suggest that DGAT1 is the predominant type, although some studies indicate that DGAT2 might be more important for TAG biosynthesis in plants like castor bean (Kroon et al., 2006).

Flax is an oilseed that substantially accumulates α-linolenic acid (α-18:3) which is an omega-3 fatty acid. Other omega-3 fatty acids include eicosapentaenoic acid (EPA) and docosahexaneoic acid (DHA) which produce beneficial health effects in humans (Simopoulos, 2002). Flaxseed oil displays chemical attributes which are advantageous for industrial applications including, for example, the production of linoleum, preservation of concrete and as an ingredient in paints and varnishes. The enzymatic activity of DGAT has been studied in isolated ER of flax developing seeds (Sorensen et al., 2005). DGAT is able to incorporate polyunsaturated fatty acids (C18:3 n-3) at higher rates compared to monounsaturated (C18:1) fatty acids. In addition, flax microsomes incorporate EPA and DHA into TAGs (Sorensen et al., 2005), highlighting the usefulness of TAG biosynthetic enzymes such as DGAT as genetic tools for engineering vegetable oils. Over-expression of DGAT in oilseed plants could potentially increase TAG production or enhance seed oil content in plants. However, since numerous enzymatic activities occur within microsomes, it is difficult to evaluate the effect of DGAT in flax using a microsome-based system. Genetically modified organisms have not achieved widespread public acceptance; however, use of native flax DGAT genes for improving the oil content through biotechnology may more readily meet stringent controls.

SUMMARY OF THE INVENTION

The present invention relates to isolated diacylglycerol acyltransferases and polynucleotide sequences encoding the DGAT enzymes; nucleic acid constructs, vectors and host cells incorporating the polynucleotide sequences; and methods of producing and using same.

In one aspect, the invention provides an isolated polynucleotide encoding a polypeptide comprising an amino acid sequence selected from:

at least 300, at least 400 or at least 500 contiguous residues of the amino acid sequence depicted in SEQ ID NO: 2 or of an amino acid sequence having at least 85% sequence identity therewith;

at least 300 contiguous residues of the amino acid sequence depicted in SEQ ID NO: 4 or of an amino acid sequence having at least 85% sequence identity therewith; or at least 300 contiguous residues of the amino acid sequence depicted in SEQ ID NO: 6 or of an amino acid sequence having at least 85% sequence identity therewith.

In one embodiment, the invention provides an isolated polynucleotide, wherein the encoded polypeptide comprises the amino acid sequence depicted in SEQ ID NO: 2.

In one embodiment, the encoded polynucleotide comprises the nucleotide sequence depicted in SEQ ID NO: 1 from nucleotide 57 to nucleotide 1580.

In one embodiment, the encoded polypeptide comprises the amino acid sequence depicted in SEQ ID NO: 4.

In one embodiment, the polynucleotide comprises the nucleotide sequence depicted in SEQ ID NO: 3 from nucleotide 1 to nucleotide 1029.

In one embodiment, the encoded polypeptide comprises the amino acid sequence depicted in SEQ ID NO: 6.

In one embodiment, the polynucleotide comprises the nucleotide sequence depicted in SEQ ID NO. 5 from nucleotide 1 to nucleotide 1048.

In one embodiment, the encoded polypeptide comprises an amino acid sequence having at least 90%, at least 95%, at least 96%, at least 97%, at least 98%, or at least 99% sequence identity to SEQ ID NO: 2.

In one embodiment, the encoded polypeptide comprises an amino acid sequence having at least 90%, at least 95%, at least 96%, at least 97%, at least 98%, or at least 99% sequence identity to SEQ ID NO: 4.

In one embodiment, the encoded polypeptide comprises an amino acid sequence having at least 90%, at least 95%, at least 96%, at least 97%, at least 98%, or at least 99% sequence identity to SEQ ID NO: 6.

In a further aspect, the invention provides a polynucleotide construct comprising any of the above polynucleotides operably linked to a promoter expressible in bacterial, yeast, fungal, mammalian or plant cells.

In a further aspect, the invention provides a vector comprising any of the above polynucleotides. In one embodiment, the invention provides a microbial cell comprising any of the above polynucleotides. In one embodiment, the microbial cell is *Saccharomyces cerevisiae*.

In a further aspect, the invention provides a transgenic plant, plant cell, plant seed, callus, plant embryo, microspore-derived embryo, or microspore, comprising any of the above polynucleotides. In one embodiment, the transgenic plant, plant cell, plant seed, callus, plant embryo, microspore-derived embryo, or microspore is selected from a flax, canola, soybean, *Camelina sativa*, mouse-ear cress, castor, sunflower, linola, oat, wheat, triticale, barley, corn or *Brachypodium distachyon* plant, plant cell, plant seed, plant embryo, or microspore.

In another aspect, the invention provides a method for producing an oil, comprising the steps of growing the above transgenic plant and recovering oil which is produced by the plant. In one embodiment, the plant is selected from a flax, canola, soybean, *Camelina sativa*, mouse-ear cress, castor, sunflower, linola, oat, wheat, triticale, barley, corn or *Brachypodium distachyon* plant.

In yet another aspect, the invention provides a method for producing a transgenic plant comprising the steps of introducing into a plant cell or a plant tissue any of the above polynucleotides to produce a transformed cell or plant tissue, and cultivating the transformed plant cell or transformed plant tissue to produce the transgenic plant. In one embodiment, the plant is selected from a flax, canola, soybean, *Camelina sativa*, mouse-ear cress, castor, sunflower, linola, oat, wheat, triticale, barley, corn or *Brachypodium distachyon* plant.

Additional aspects and advantages of the present invention will be apparent in view of the description, which follows. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The invention will now be described in relation to the drawings in which:

FIGS. 1A, 1B and 1C show a contig of LuDGAT1 obtained by assembling six isolated fragments (amplicon1 (SEQ ID NO: 28), amplicon2 (SEQ ID NO:29), RT-PCR (SEQ ID NO:30), 3' RACEm (SEQ ID NO:33), 5' RACE (SEQ ID NO:31) and 5' RACEB (SEQ ID NO:32)).

FIG. 3 shows the cDNA sequence of LuDGAT1 (SEQ ID NO:1) and the predicted polypeptide sequence (SEQ ID NO:2).

FIGS. 4A, 4B, 4C and 4D show an amino acid alignment of plant DGAT1 with the accession numbers and species indicated for each sequence, black highlight indicating identical residues and grey highlight indicating blocks of conserved residues.

DETAILED DESCRIPTION OF PREFERRED EMBODIMENTS

Figure 2:
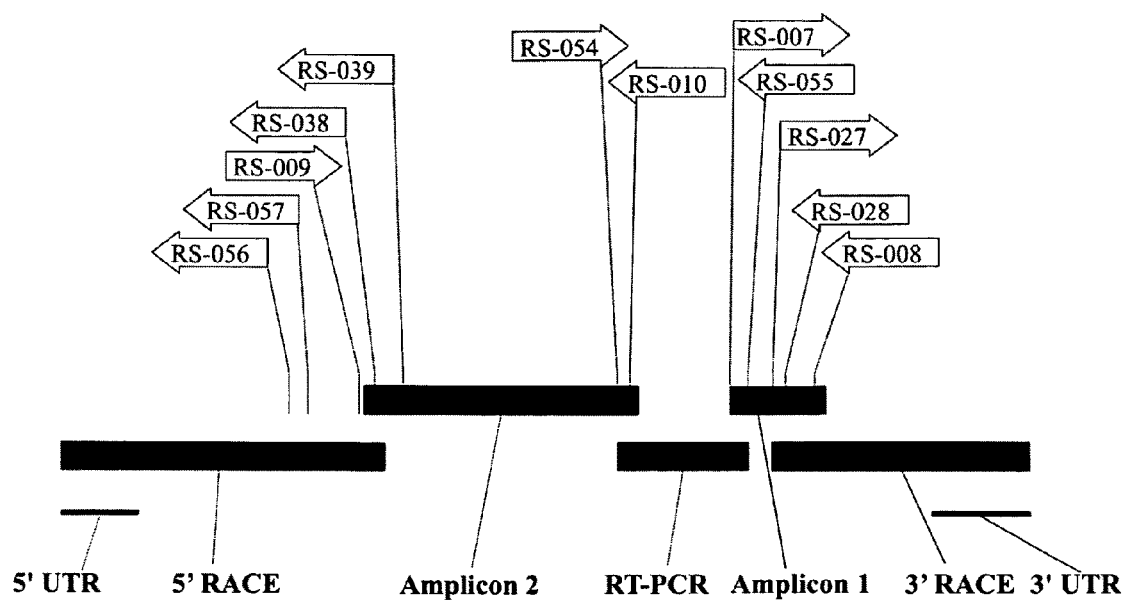
FIG. 2 is a schematic drawing of the LuDGAT1 cDNA contig. The fragments obtained by PCR are represented by the rectangles. The 5' and 3' untranslated regions are designated by lines. The annealing position and orientation of the oligonucleotides are described on the top.

As will be apparent to those skilled in the art, various modifications, adaptations and variations of the foregoing specific disclosure can be made without departing from the scope of the invention claimed herein. The various features and elements of the described invention may be combined in a manner different from the combinations described or claimed herein, without departing from the scope of the invention.

To facilitate understanding of the invention, the following definitions are provided.

"Isolated" means that a substance or a group of substances is removed from the coexisting materials of its natural state.

A "polynucleotide" is a linear sequence of ribonucleotides (RNA) or deoxyribonucleotides (DNA) in which the 3' carbon of the pentose sugar of one nucleotide is linked to the 5' carbon of the pentose sugar of another nucleotide. The deoxyribonucleotide bases are abbreviated as "A" deoxyadenine; "C" deoxycytidine; "G" deoxyguanine; "T" deoxythymidine; "I" deoxyinosine. Some oligonucleotides described herein are produced synthetically and contain different deoxyribonucleotides occupying the same position in the sequence. The blends of deoxyribonucleotides are abbreviated as "W" A or T; "Y" C or T; "H" A, C or T; "K" G or T; "D" A, G or T; "B" C, G or T; "N" A, C, G or T.

A "polypeptide" is a linear sequence of amino acids linked by peptide bonds. The amino acids are abbreviated as "A" alanine; "R" arginine; "N" asparagine; "D" aspartic acid; "C" cysteine; "Q" glutamine; "E" glutamic acid; "G" glycine; "H" histidine; "I" isoleucine; "L" leucine; "K" lysine; "M" methionine; "F" phenylalanine; "P" proline; "S" serine; "T" threonine; "W" tryptophan; "Y" tyrosine and "V" valine.

"Downstream" means on the 3' side of a polynucleotide while "upstream" means on the 5' side of a polynucleotide.

"Expression" refers to the transcription of a gene into RNA (rRNA, tRNA) or messenger RNA (mRNA) with subsequent translation into a protein.

A "promoter" is a polynucleotide usually located within 20 to 5000 nucleotides upstream of the initiation of translation site of a gene. The "promoter" determines the first step of expression by providing a binding site to DNA polymerase to initiate the transcription of a gene. The promoter is said to be "inducible" when the initiation of transcription occurs only when a specific agent or chemical substance is presented to the cell. For instance, the GAL "promoter" from yeast is "inducible by galactose," meaning that this GAL promoter allows initiation of transcription and subsequent expression only when galactose is presented to yeast cells.

A "coding sequence" or "coding region" or "open reading frame (ORF)" is part of a gene that codes for an amino acid sequence of a polypeptide.

A "complementary sequence" is a sequence of nucleotides which forms a duplex with another sequence of nucleotides according to Watson-Crick base pairing rules where "A" pairs with "T" and "C" pairs with "G." For example, for the polynucleotide 5'-AATGCCTA-3' the complementary sequence is 5'-TAGGCATT-3'.

A "cDNA" is a polynucleotide which is complementary to a molecule of messenger RNA mRNA. The "cDNA" is formed of a coding sequence flanked by 5' and 3' untranslated sequences.

"DGAT" is an enzyme of the class EC 2.3.1.20 which catalyzes the reaction: acyl-CoA+sn-1,2-diacylglycerol→CoA+triacylglycerol. Alternative names include: diacylglycerol O-acyltransferase, diacylglycerol acyltransferase, diglyceride acyltransferase and acylCoA:diacylglycerol acyltransferase.

A polypeptide having "DGAT activity" is a polypeptide that has, to a greater or lesser degree, the enzymatic activity of DGAT.

A "recombinant" polynucleotide is a novel polynucleotide sequence formed in vitro through the ligation of two DNA molecules.

A "construct" is a polynucleotide which is formed by polynucleotide segments isolated from a naturally occurring gene or which is chemically synthesized. The "construct" which is combined in a manner that otherwise would not exist in nature, is usually made to achieve certain purposes. For instance, the coding region from "gene A" can be combined with an inducible promoter from "gene B" so the expression of the recombinant construct can be induced.

"Transformation" means the directed modification of the genome of a cell by external application of a polynucleotide, for instance, a construct. The inserted polynucleotide may or may not integrate with the host cell chromosome. For example, in bacteria, the inserted polynucleotide usually does not integrate with the bacterial genome and might replicate autonomously. In plants, the inserted polynucleotide integrates with the plant chromosome and replicates together with the plant chromatin.

A "transgenic" organism is the organism that was transformed with an external polynucleotide. The "transgenic" organism encompasses all descendants, hybrids and crosses thereof, whether reproduced sexually or asexually and which continue to harbor the foreign polynucleotide.

A "vector" is a polynucleotide that is able to replicate autonomously in a host cell and is able to accept other polynucleotides. For autonomous replication, the vector contains an "origin of replication." The vector may contain a "selectable marker" that confers the host cell resistance to certain environment and growth conditions. For instance, a vector that is used to transform bacteria usually contains a certain antibiotic "selectable marker" which confers the transformed bacteria resistance to such antibiotic.

Two polynucleotides or polypeptides are "identical" if the sequence of nucleotides or amino acids, respectively, in the two sequences is the same when aligned for maximum correspondence as described here. Sequence comparisons between two or more polynucleotides or polypeptides can be generally performed by comparing portions of the two sequences over a comparison window which can be from about 20 to about 200 nucleotides or amino acids, or more. The "percentage of sequence identity" may be determined by comparing two optimally aligned sequences over a comparison window, wherein the portion of a polynucleotide or a polypeptide sequence may include additions (i.e., insertions) or deletions (i.e., gaps) as compared to the reference sequence. The percentage is calculated by determining the positions at which identical nucleotides or identical amino acids are present, dividing by the number of positions in the window and multiplying the result by 100 to yield the percentage of sequence identity. Polynucleotide and polypeptide sequence alignment may be performed by implementing specialized algorithms or by inspection. Examples of sequence comparison and multiple sequence alignment algorithms are: BLAST and ClustalW softwares. Identity between nucleotide sequences can also be determined by DNA hybridization analysis, wherein the stability of the double-stranded DNA hybrid is dependent on the extent of base pairing that occurs. Conditions of high temperature and/or low salt content reduce the stability of the hybrid, and can be varied to prevent annealing of sequences having less than a selected degree of homology. Hybridization methods are described in Ausubel et al. (1995).

The invention provides isolated DGAT1 and DGAT2 polynucleotides and polypeptides. DGAT1 and DGAT2 polynucleotides include, without limitation (1) single- or double-stranded DNA, such as cDNA or genomic DNA including sense and antisense strands; and (2) RNA, such as mRNA. DGAT1 and DGAT2 polynucleotides include at least a coding sequence which codes for the amino acid sequence of the specified DGAT polypeptide, but may also include 5' and 3' untranslated regions and transcriptional regulatory elements such as promoters and enhancers found upstream or downstream from the transcribed region.

In one embodiment, the invention provides a DGAT1 polynucleotide which is a cDNA comprising the nucleotide sequence depicted in SEQ ID NO: 1, and which was isolated from *Linum usitatissimum*. The cDNA is 1778 base pairs in length including a coding region of 1524 base pairs (SEQ ID NO: 1 from nucleotide 57 to nucleotide 1580) and untranslated 5' and 3' regions of 56 and 198 base pairs, respectively. The DGAT1 encoded by the coding region (designated as LuDGAT1, SEQ ID NO: 2) is a 507 amino acid polypeptide with a predicted molecular weight of 58,012 Daltons and an isoelectric point of 8.74.

In one embodiment, the invention provides a DGAT2 polynucleotide which is a coding region comprising the nucleotide sequence depicted in SEQ ID NO: 3, which was also isolated from *Linum usitatissimum*. The coding region is 1029 base pairs in length and the DGAT2 encoded by the coding region (designated as LuDGAT2A, SEQ ID NO: 4) is a 343 amino acid polypeptide with a predicted molecular weight of 38,201 Daltons and an isoelectric point of 9.28.

In one embodiment, the invention provides a DGAT2 coding region comprising the nucleotide sequence depicted in SEQ ID NO: 5 and which was isolated from *Linum usitatissimum*. The coding region is 1048 base pairs in length and the DGAT2 encoded by the coding region (designated here by LuDGAT2B, SEQ ID NO: 6) is a 349 amino acid polypeptide with a predicted molecular weight of 38,737 Daltons and an isoelectric point of 9.18.

Those skilled in the art will recognize that the degeneracy of the genetic code allows for a plurality of polynucleotides to encode for identical polypeptides. Accordingly, the invention includes polynucleotides of SEQ ID NOS: 1, 3 and 5, and variants of polynucleotides encoding polypeptides of SEQ ID NOS: 2, 4 and 6. In one embodiment, polynucleotides having at least 85%, at least 90%, at least 95%, at least 96%, at least 97%, at least 98%, or at least 99% sequence identity to the nucleotide sequences depicted in SEQ ID NO: 1, SEQ ID NO: 3 and SEQ ID NO: 5 are included in the invention. Methods for isolation of such polynucleotides are well known in the art (see for example, Ausubel et al., 1995).

In one embodiment, the invention provides isolated polynucleotides which encode polypeptides having DGAT activity and which comprise amino acid sequences having at least 85%, at least 90%, at least 95%, at least 96%, at least 97%, at least 98%, or at least 99% sequence identity to the amino acid sequences depicted in SEQ ID NO: 2; SEQ ID NO: 4 and SEQ ID NO: 6.

In one embodiment, the invention provides isolated polynucleotides which encode polypeptides having DGAT activity and which comprise amino acid sequences having a length of at least 300, at least 400 or at least 500 contiguous residues of the amino acid sequence depicted in SEQ ID NO: 2. In one embodiment, the invention provides isolated polynucleotides which encode polypeptides having DGAT activity and which comprise amino acid sequences having a length of at least 300 contiguous residues of the amino acid sequence depicted in SEQ ID NO: 4. In one embodiment, the invention provides isolated polynucleotides which encode polypeptides having DGAT activity and which comprise amino acid sequences having a length of at least 300 contiguous residues of the amino acid sequence depicted in SEQ ID NO: 6.

The above described polynucleotides of the invention may be used to express polypeptides in recombinantly engineered cells including, for example, bacterial, yeast, fungal, mammalian or plant cells. In one embodiment, the invention provides polynucleotide constructs, vectors and cells comprising DGAT polynucleotides. Those skilled in the art are knowledgeable in the numerous systems available for expression of a polynucleotide. All systems employ a similar approach, whereby an expression construct is assembled to include the protein coding sequence of interest and control sequences such as promoters, enhancers, and terminators, with signal sequences and selectable markers included if desired. Briefly, the expression of isolated polynucleotides encoding polypeptides is typically achieved by operably linking, for example, the DNA or cDNA to a constitutive or inducible promoter, followed by incorporation into an expression vector. The vectors can be suitable for replication and integration in either prokaryotes or eukaryotes. Typical expression vectors include transcription and translation terminators, initiation sequences, and promoters useful for regulation of the expression of the DNA. High level expression of a cloned gene is obtained by constructing expression vectors which contain a strong promoter to direct transcription, a ribosome binding site for translational initiation, and a transcription/translation terminator. Vectors may further comprise transit and targeting sequences, selectable markers, enhancers or operators. Means for preparing vectors are well known in the art. Typical vectors useful for expression of polynucleotides in plants include for example, vectors derived from the Ti plasmid of *Agrobacterium tumefaciens* and the pCaM-VCN transfer control vector. Promoters suitable for plant cells include for example, the nopaline synthase, octopine synthase, and mannopine synthase promoters, the caulimovirus promoters and seed specific promoters, such as *Brassica napus* napin promoter.

Those skilled in the art will appreciate that modifications (i.e., amino acid substitutions, additions, deletions and post-translational modifications) can be made to a polypeptide of the invention without eliminating or diminishing its biological activity. Conservative amino acid substitutions (i.e., substitution of one amino acid for another amino acid of similar size, charge, polarity and conformation) or substitution of one amino acid for another within the same group (i.e., nonpolar group, polar group, positively charged group, negatively charged group) are unlikely to alter protein function adversely. Some modifications may be made to facilitate the cloning, expression or purification. Variant DGAT polypeptides may be obtained by mutagenesis of the polynucleotides depicted in SEQ ID NOS: 1, 3 and 5 using techniques known in the art including, for example, oligonucleotide-directed mutagenesis, region-specific mutagenesis, linker-scanning mutagenesis, and site-directed mutagenesis by PCR (Ausubel et al., 1995). Variant DGAT polypeptides can be tested for DGAT activity by the assay described in Example 4.

Various methods for transformation or transfection of cells are available. For prokaryotes, lower eukaryotes and animal cells, such methods include for example, calcium phosphate precipitation, fusion of the recipient cells with bacterial protoplasts containing the DNA, treatment of the recipient cells with liposomes containing the DNA, DEAE dextran, electroporation, biolistics and microinjection. The transfected cells are cultured, and the produced DGAT polypeptides may be isolated and purified from the cells using standard techniques known in the art. Accordingly, in one embodiment, the invention provides methods for producing DGAT in yeast as described in Example 4. Various industrial strains of microorganisms including for example, *Aspergillus, Pichia pastoris, Saccharomyces cerevisiae, E. coli, Bacillus subtilis*) may be used to produce DGAT polypeptides. In one embodiment, the microbial cell is *Saccharomyces cerevisiae*.

Methods for transformation of plant cells include for example, electroporation, PEG poration, particle bombardment, *Agrobacterium tumefaciens*- or *Agrobacterium rhizogenes*-mediated transformation, and microinjection. The transformed plant cells, seeds, callus, embryos, microspore-derived embryos, microspores, organs or explants are cultured or cultivated using standard plant tissue culture techniques and growth media to regenerate a whole transgenic plant which possesses the transformed genotype. Transgenic *Camelina sativa* plants are regenerated as is disclosed in U.S. patent application Ser. No. 12/290,379 and 12/228,791. Transgenic plants may pass polynucleotides encoding DGAT polypeptides to their progeny, or can be further crossbred with other species. Accordingly, in one embodiment, the invention provides methods for producing transgenic plants, plant cells, callus, seeds, plant embryos, microspore-derived embryos, and microspores comprising DGAT polynucleotides.

In one embodiment, the invention provides transgenic plants, plant cells, callus, seeds, plant embryos, microspore-derived embryos, and microspores comprising DGAT polynucleotides. Plant species of interest for transformation include, without limitation, crops used for commercial oil production such as, for example, flax (*Linum* spp.), canola, soybean (*Glycine* and *Soja* spp.), *Camelina sativa*, mouse-ear cress (*Arabidopsis thaliana*), castor, sunflower and linola. In one embodiment, the plant is a flax plant. In one embodiment, the plant is a canola plant. In yet another embodiment the plant is *Camelina sativa* plant. Transgenic *Camelina sativa* plants preferably do not contain selection markers. It will be appreciated by those skilled in the art that the plant species for transformation are not limited to crops grown for commercial oil production. Such additional plant species include, without limitation, oats, wheat, triticale, barley, corn and *Brachypodium distachyon*.

The DGAT polynucleotides, polypeptides, and methods of the invention are useful in a wide range of agricultural, industrial and nutritional applications. Transgenic plants with increased seed oil content can be developed; for example, transgenic plants which have the unique preference of incorporating omega-3 fatty acids into TAGs. Co-expression of LuDGAT1 and LuDGAT2 with a delta-15 dessaturase gene to feed LuDGAT with a polyunsaturated fatty acid may be conducted in plant species which do not normally produce C18:3 fatty acid. Recombinant expression of DGAT may be achieved in plants which are typically not grown for commercial oil production, resulting in development of new cultivars which produce oil having a similar composition to flaxseed oil.

Further, the DGAT polynucleotides and polypeptides may be used in the industrial production and recovery of oil products using recombinant technology such as transformed bacterial, yeast or fungal cells. Transformed cells may be engineered to accumulate omega-3 fatty acids in TAGs.

The DGAT polynucleotides and polypeptides may be incorporated into human food and animal feed applications to provide healthier products or to improve the fat quality of products. For example, a healthier dietary oil having a fatty acid profile which reduces the risk of coronary heart disease and decreases plasma cholesterol may be developed for humans. Livestock are unable to convert n-6 fatty acids into n-3 fatty acids since they lack an n-3 fatty acid desaturase gene. However, co-expression of LuDGAT1 and/or LuDGAT2 with fat-1 desaturase gene in livestock may increase the amount of n-3 fatty acids.

The Examples provided below are not intended to be limited to these examples alone, but are intended only to illustrate and describe the invention rather than limit the claims that follow.

EXAMPLES

Example 1

Isolation of RNA from Flax Embryos

Flax plants (*Linum usitatissimum* L. cv AC Emerson) were grown in greenhouse conditions, irrigated at 2-3 day intervals and fertilized weekly with 1% Peters 20-20-20 general purpose fertilizer (Scotts, Marysville, Ohio). Flax embryos were isolated from developing seeds and RNA was obtained using 350 mg of embryos frozen in liquid nitrogen and ground with mortar and pestle. Ground embryos were transferred to a 2 ml tube and 500 µl of extraction buffer (50 mM TrisHCl pH 9.0, 200 mM NaCl, 1% Sarkosyl, 20 mM EDTA, and 5 mM DTT) was added, mixing with a vortex. 500 µl of phenol chloroform mixture (Sigma-Aldrich Ltd, Oakville, ON) was added and mixed with a vortex. The sample was centrifuged for 5 minutes at 12000 g at 4° C. The aqueous upper phase was transferred to a new tube and 1 ml of Trizol reagent (Gibco, Burlington, ON, Canada) was added, followed by addition of 250 µl of chloroform. The sample was mixed with a vortex and centrifuged for 5 minutes at 12000 g at 4° C. The aqueous upper phase (750 µl) was transferred to a new tube and 500 µl of chloroform was added and mixed in a vortex. The sample was centrifuged for 5 minutes at 12000 g at 4° C. The upper phase (600 µl) was transferred to a new tube and the RNA was precipitated with addition of 60 µl of sodium acetate (3M) and 1.2 ml of ethanol. The sample was incubated at −80° C. for 1 hour and centrifuged for 20 minutes at 14000 g at 4° C. The RNA pellet was washed with 70% ethanol, followed by brief centrifugation (2 minutes at 14000 g at 4° C.) and dried with a vacufuge (Ependorf, Westbury, N.Y., U.S.). The RNA pellet was diluted in 50 µl of water and centrifuged for 20 minutes at 14000 g at 4° C. Total RNA was quantified by using a Nanodrop™ spectrophotometer (NanoDrop Technologies, Wilmington, Del., U.S.).

Example 2

Isolation of LuDGAT1 cDNA

Recombinant DNA techniques such as digestion by restriction endonucleases, ligation and plasmid preparation were performed as described by Ausubel et al. (1995). First strand synthesis of complementary DNA (cDNA) was produced by reverse transcription. Five micrograms of flax embryo RNA were mixed with 50 pmoles of oligonucleotide 5'-GGC-CACGCGTCGACTAGTACTTTTTTTTTTTTTTTTVN-3' (oligodT adaptor; SEQ ID NO: 7) and 1 mM of dNTP in a total volume of 10 µl. The mixture was incubated at 65° C. for 5 minutes and immediately cooled on ice for 2 minutes. A total volume of 10 µl of cDNA synthesis mix was added. This mix consisted of 2× transcriptase buffer, 10 mM of $MgCl_2$, 20 mM of DTT and 200 units of Superscript II (Invitrogen, Burlington, ON). The reaction was incubated at 50° C. for 50 minutes followed by enzyme inactivation at 85° C. for 5 minutes. The reaction was cooled to 37° C. and incubated at this temperature for 20 minutes in the presence of 4 units of RNAseH (Invitrogen) and 1 unit of RNAseT1 (Ambion, Austin, Tex., U.S.) to remove the mRNA strand from RNA-DNA duplexes and single-stranded RNA, respectively. The synthesized cDNA was stored at −20° C.

Polymerase chain reaction (PCR) was performed using 200 µM of each dNTP, 0.1 volumes of PCR reaction buffer, and varying amounts of oligonucleotide, polymerases, DNA template and $MgSO_4$ or $MgCl_2$, according to the application in a final volume of 50 µl. The general PCR thermal cycling conditions were: 2 minutes preheat at 94° C. followed by 30 cycles of 94° C. denaturing for 30 seconds, 55° C. annealing for 30 seconds and 72° C. or 68° C. extension for 1 to 2 minutes. After the final cycle, the PCR reactions were incubated for 10 minutes at 72° C. or 68° C. for further extension and cooled to 10° C. until used for analysis.

The degenerate oligonucleotides 5'-GARTTYTAYCAN-GAYTGGTGG-3' (RS-007; SEQ ID NO: 8), 5'-GGNAC-NGCNATRCANARYTCRTG-3' (RS-008; SEQ ID NO: 9), 5'-GARAANYTNATGAARTAYGG-3' (RS-009; SEQ ID NO: 10) and 5'-TANTGYTCNATDATRAANCCCAT-3' (RS-010; SEQ ID NO: 11) were designed based on several plant DGAT1 sequences available in public databases. Such oligonucleotides, which provide limited specificity to the template, were used on PCR amplification of two different segments of DGAT1 using cDNA previously described as a template. These two DNA segments were sequenced using BigDye Version 3.1 dye terminator cycle sequencing kit (Applied Biosystems, Streetsville, ON, Canada). Samples were analyzed in an automatic sequencer (Applied Biosystems 373A Sequencer) at the University of Alberta Molecular Biology Service Unit (MBSU). Sequencing chromatograms were trimmed and assembled using Contig Express and "BLASTed" (Altschul et al., 1995; www.ncbi.nlm.nih.gov/BLAST) against public DNA databases.

Sequences from these two DNA segments, here named amplicon1 and amplicon2 (FIGS. 1 and 2), were used to design specific oligonucleotides to LuDGAT1 cDNA. These specific oligonucleotides were used in rapid amplification of cDNA ends (RACE) and reverse transcription-PCR (RT-PCR) amplification reactions to obtain the full nucleotide sequence of DGAT1.

3' RACE was obtained using the oligonucleotides 5'-GC-CATATCTATTTCCCATGTCTGCGG-3' (RS027; SEQ ID NO: 12) and 5'-GGCCACGCGTCGACTAGTAC-3' (adaptor; SEQ ID NO: 13) using cDNA previously described as template. For 5' RACE flax cDNA was produced using the oligonucleotide 5'-CACTGGAAGTGTTAGACAG-3' (RS-039; SEQ ID NO: 14) using the same conditions described before. The cDNA and the 3' end were tailed with dCTP using Terminal deoxynucleotidyl Transferase (TdT). 5'-RACE was amplified using the oligonucleotides 5'-GGCCACGCGTC-GACTAGTACGGGGGGGGGGGGGGGGGGN-3' (oligo dG adaptor; SEQ ID NO: 15) and 5'-ACTGAACCAGAAGCCT-GTC-3' (RS-038; SEQ ID NO: 16). This reaction yielded a truncated 5' RACE product. A second 5'-RACE (here called 5'RACEB) was performed by producing flax embryo cDNA with the oligonucleotide 5'-CGGAACTAAGCGGACTCTC-3' (RS-057; SEQ ID NO: 17) and tailing with dCTP. 5'-RA-CEB was performed using 5'-GGCACGGAAGGGCGG-TAAG-3' (RS-056; SEQ ID NO: 18) and oligo dG adaptor. Sequences obtained from 5' and 3' RACE products were aligned with amplicon1 and amplicon2 sequences (FIG. 2).

RT-PCR of the DNA segment between amplicon1 and amplicon2 (FIG. 1) was performed using the oligonucleotides 5'-CAAGTTAGTAATATTTACAGGC-3', (RS-054; SEQ ID NO: 19) and 5'-TCCACATTCTCCAGTATTCTTC-3' (RS-055; SEQ ID NO: 20) (FIGS. 1 and 2) and a cDNA from flax embryos previously described. The RT-PCR product was sequenced and aligned with sequences from other LuDGAT1 segments previously obtained (FIG. 2).

The coding region of LuDGAT1 was obtained through RT-PCR using the oligonucleotides 5'-ATTAGGATCCGAC-CATGGGCGTGCTCGACACTCCTGACAATC-3' (RS-100; SEQ ID NO: 21) and 5'-TTTAAGCTTGATTC-CATCTTTCCCATTCCTG-3' (RS-101; SEQ ID NO: 22) and flax embryo cDNA as template. The RT-PCR product of LuDGAT1 coding region was sequenced and analyzed.

Example 3

Analysis of LuDGAT1 Sequence

DNA sequences were analyzed using VectorNTi™ Advance 10.1.1 (Invitrogen) software package. Amino acid and DNA alignments were performed with AlignX, and phylogenetic trees were visualized using Tree View™ version 1.6.6.

Figure 4A:
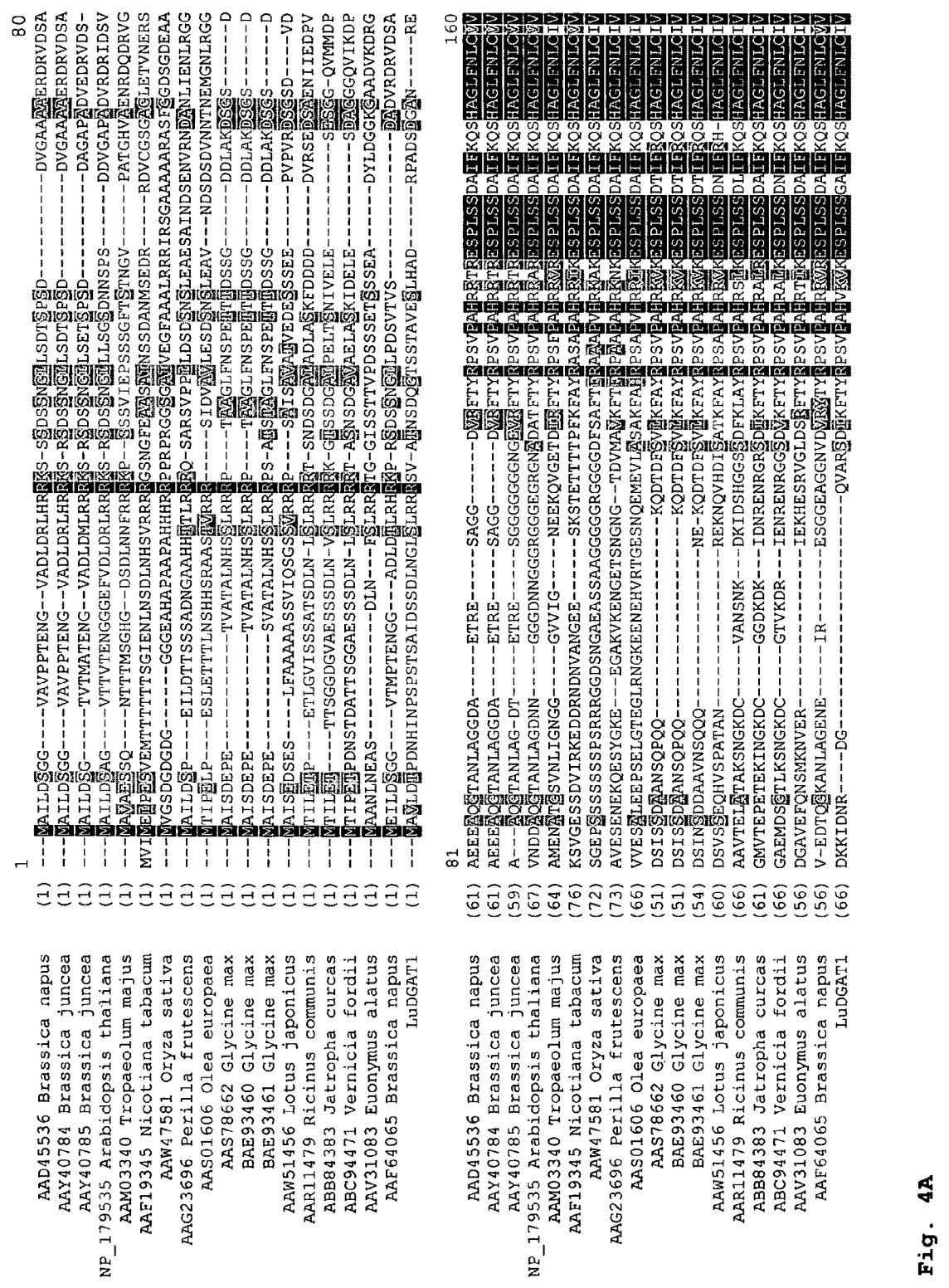
Figure 4B:
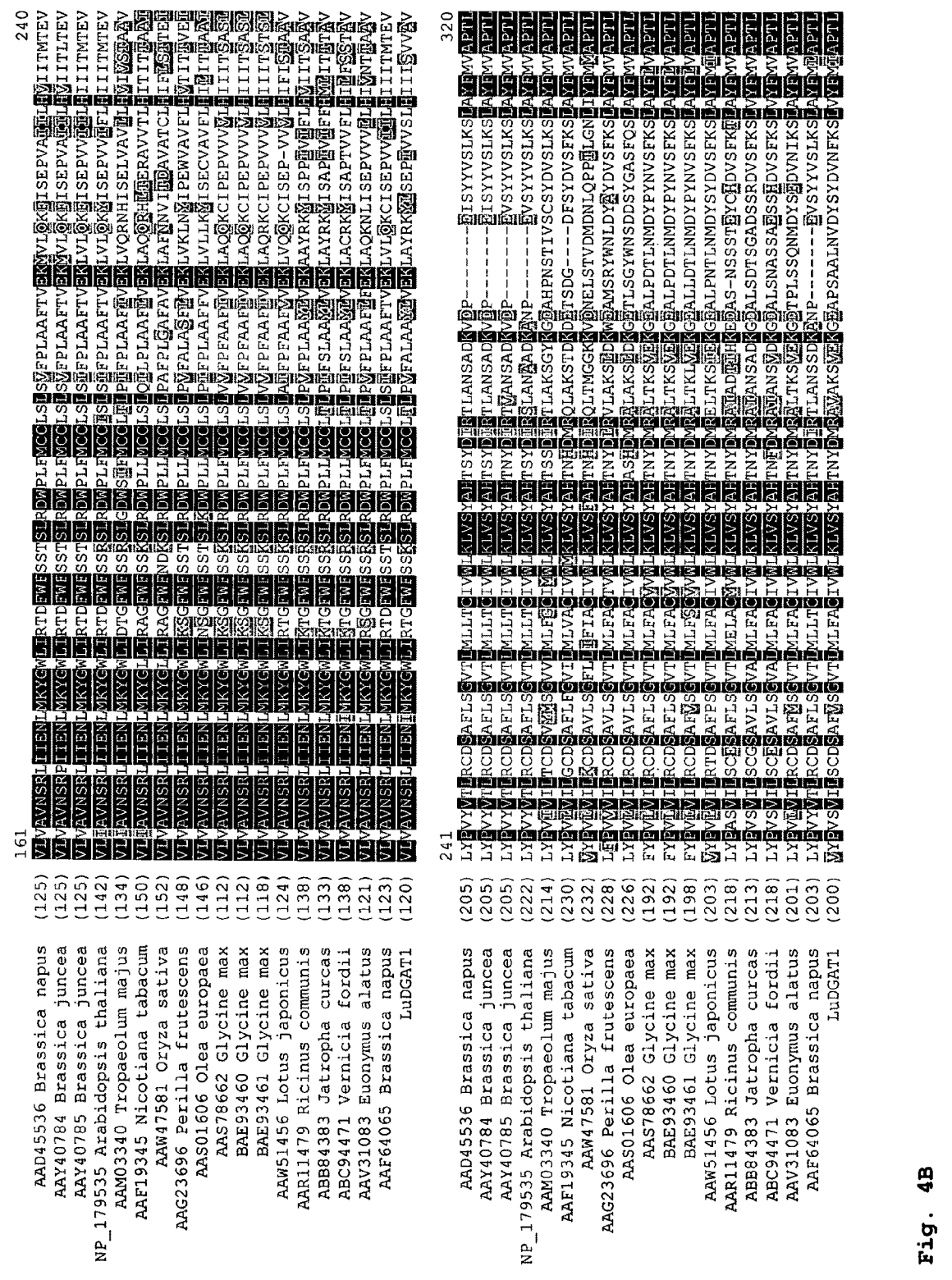
Figure 4C:
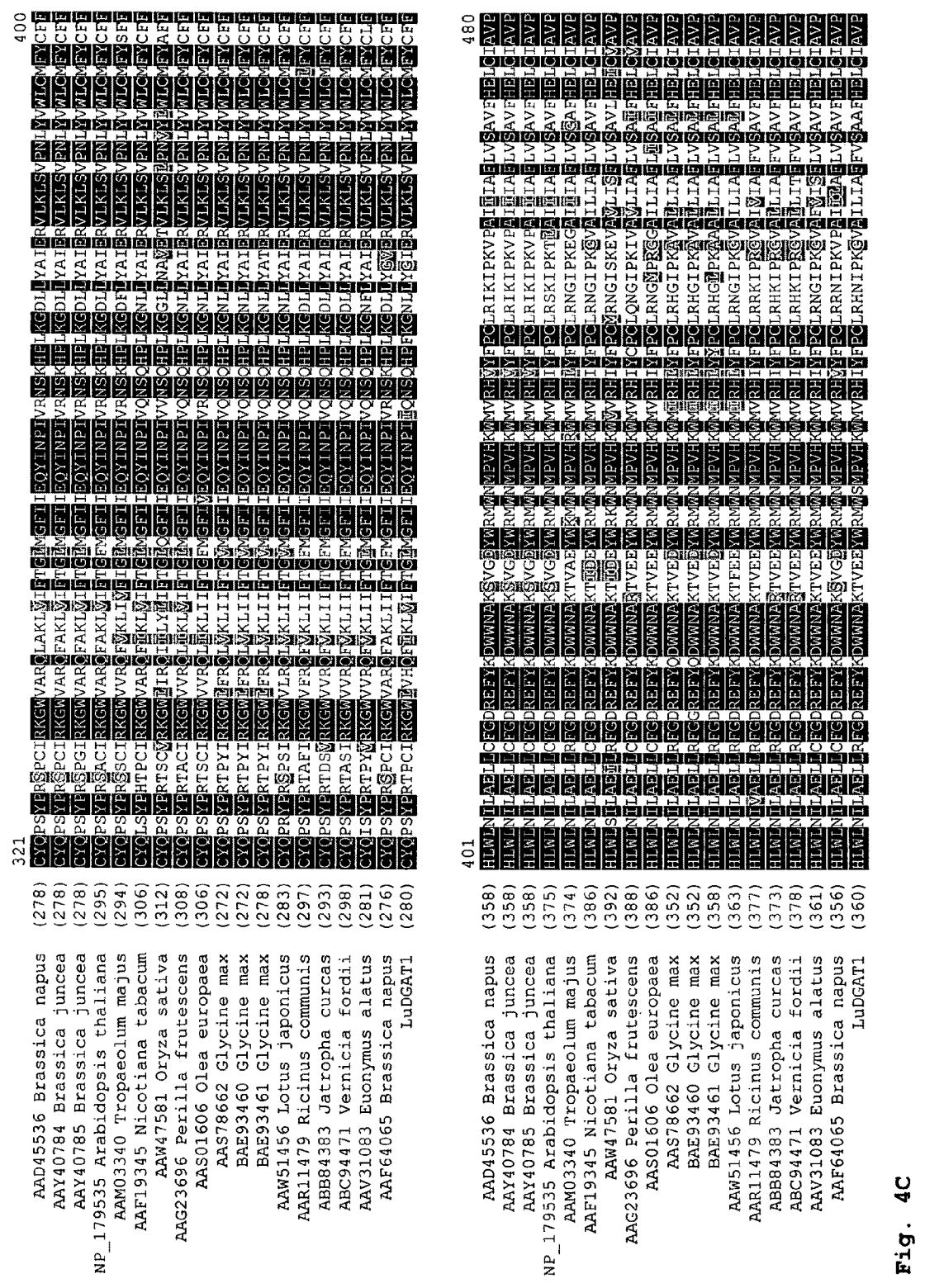
Figure 5:
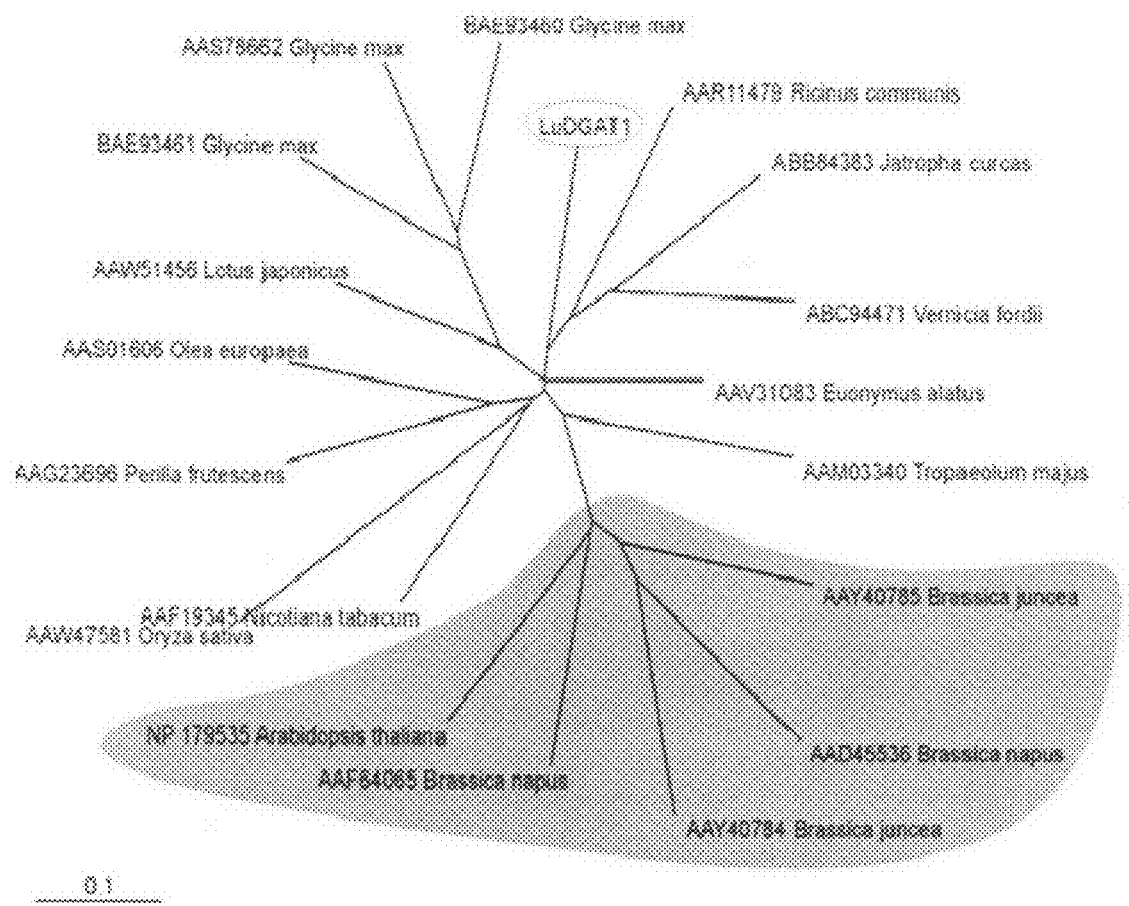
FIG. 5 shows a phylogenetic tree of plant DGAT1 with the accession numbers indicated for each plant species and oilseed members of the Cruciferae family highlighted in grey.

The full sequence of DGAT1 cDNA has 1778 base pairs with an open reading frame of 1521 base pairs comprising 507 amino acids with a molecular weight of 58.02 kDa. The predicted LuDGAT1 polypeptide, obtained by analysis of the ORF of LuDGAT1 cDNA (FIG. 3), was compared to other DGAT polypeptides from plants available in public databases. This comparison showed that LuDGAT1 is 74% identical with *Vernicia fordii* (tung tree), 75% with *Jatropha curcas*, 73% with *Euonymus alatus* (burning bush) and 65% with *Brassica napus* but only 40% with *Mus musculus* and 39% with *Homo sapiens*. An alignment of LuDGAT1 with several other plant DGAT1 (FIG. 4) showed many similarities and also some unique features. When compared to DGAT1 from other plants, LuDGAT1 presents the polypeptide "APSAALNV" (SEQ ID NO: 23) in the region between positions 253 and 259, which is absent in DGAT1 from cruciferaceae (*Arabidopsis* and *Brassica* sp.). A phylogenetic tree obtained with the previous alignment (FIG. 5) shows higher similarity between LuDGAT1 and *Vernicia fordii*, *Jatropha curcas* and *Ricinus communis*, compared to *Oryza sativa*, *Brassica napus* and *Arabidopsis thaliana*. LuDGAT presents unique features such as the substitution of the aspartic acid with glycine at position 103 in the conserved motif "ESPLSSD" (SEQ ID NO: 24). In position 271, the motif "LAYF" (SEQ ID NO: 25) is modified to "LVYF" (SEQ ID NO: 26). In the conserved motif "MWNMPVH" (SEQ ID NO: 27) present in other plant DGATs, the conserved asparagine in position 395 is substituted by a serine. These variations could reflect unique characteristics of LuDGAT1 enzymatic activity and specificity.

Figure 6:
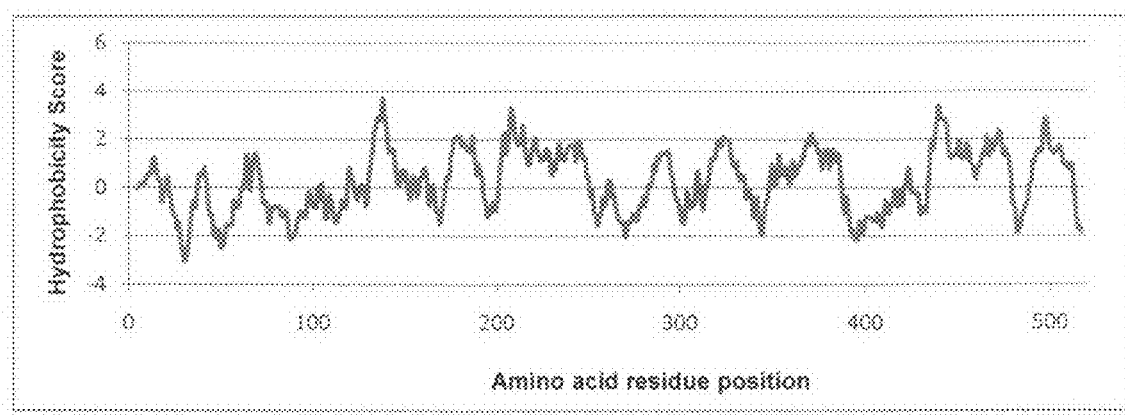
FIG. 6 shows a hydropathy plot of LuDGAT1 polypeptide using the Kyte and Doolittle scale (Kyte and Doolittle, 1982).

LuDGAT presents a hydrophilic N-terminus and several hydrophobic regions (FIG. 6), which is typical in other DGAT1 proteins. The first 80 residues present much higher variability compared to the rest of the protein, which is a characteristic found in other DGATs. Nine transmembrane regions were predicted in LuDGAT1 using TMPRED (http://www.ch.embnet.org/) (TM1 from 127 to 148, TM2 from 172 to 191, TM3 from 204 to 225, TM4 from 230 to 252, TM 5 from 311 to 331, TM 6 from 360 to 380, TM7 from 432 to 457, TM8 from 461 to 477 and TM9 from 493 to 511). Motif searches revealed that LuDGAT1 has a membrane bound O-acyl transferase (MBOAT) motif (pfam03062.12) which is present in a variety of acyltransferase enzymes such as DGAT1.

Example 4

Expression of LuDGAT1 in Yeast

The LuDGAT1 coding region was subcloned into pYES2.1/V5-HIS vector under control of GAL1 promoter which is inducible by galactose. A yeast consensus sequence for initiation of translation, composed of 5-('g/a) nnatgg-3', was introduced and the second amino acid codon was changed from gcg (A) to ggg (G). The translation stop sequence 5'-tga-3' was removed in order to fuse LuDGAT1 in frame with V5 and HIS tags. The recombinant plasmid, called pYES LuDGAT1, was introduced into *Saccharomyces cerevisiae* strain H1246. A single colony containing pYES LuDGAT1 was inoculated in medium containing 2% glucose and grown overnight. The expression of LuDGAT1 was induced with medium containing 2% galactose. The same procedure was performed for pYES BnDGAT1 which contains the cDNA encoding DGAT1 from *Brassica napus* (Nykiforuk et al., 2002). pYES BnDGAT1 was used to compare the activity of another plant DGAT to LuDGAT1. Microsomes were extracted from induced yeast cells as described by Urban et al. (1994) and DGAT activity was determined by measuring the incorporation of $^{14}$C-oleyl-CoA into TAG. As *S. cerevisiae* strain H1246 is deficient in TAG biosynthesis (Sandager et al., 2002), the DGAT activity observed results only from the recombinant DGAT expressed.

Figure 7:
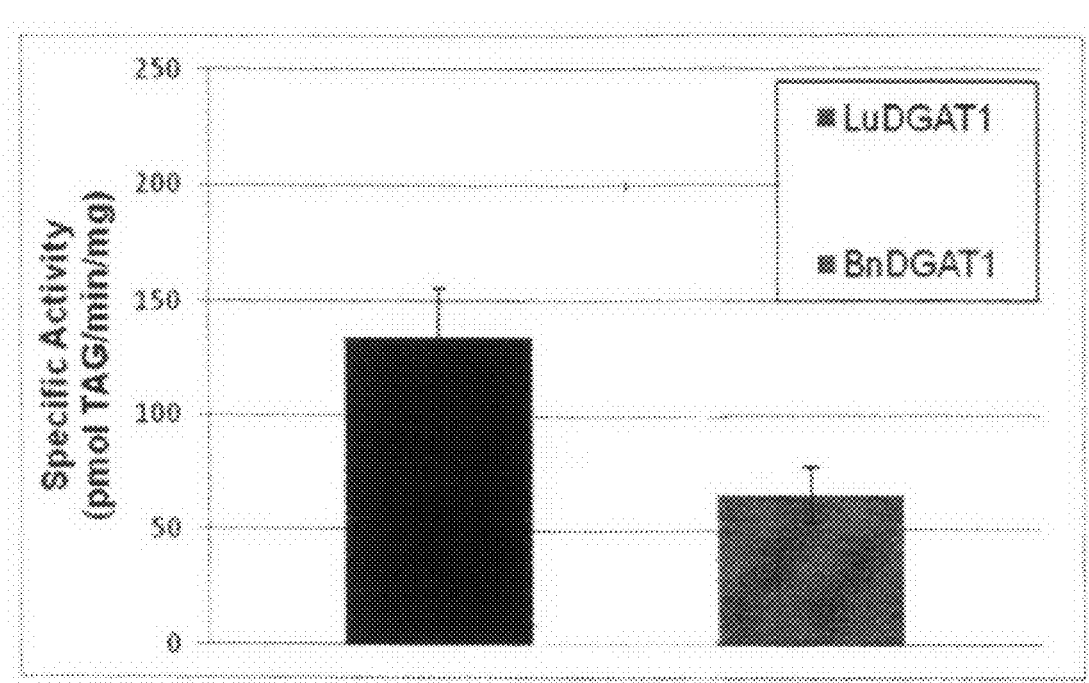
FIG. 7 is a graph showing the specific activity of type-1 DGAT in microsomes from yeast expressing plant type-1 DGAT.

DGAT assays were performed according to Byers et al. (1999). The standard reaction mixture (60 µL) consisted of 0.2 M Hepes-NaOH buffer (pH 7.4) containing 0.15 mg BSA/mL, 20 mM MgSO$_4$, 330 µM sn-1,2-diolein in 0.2% (wt/vol) Tween™ 20, 15 µM [1-$^{14}$C] oleoyl-CoA (56 mCi/mmo) and microsomal protein (80-120 µg). The reaction was performed for 15 min at 30° C. Each reaction mixture was spotted directly onto a silica gel thin layer chromatography plate, which was developed in hexane/ether (80:20, vol/vol). Sections of silica containing TAG were scraped into scintillation vials, combined with 5 mL Ecolite(+) and assayed for radioactivity in a liquid scintillation counter. As observed in FIG. 7, LuDGAT1 has comparable DGAT specific activity to BnDGAT1.

Example 5

Transformation of *Camelina sativa* cv. Calena with *Agrobacterium tumefaciens* strain C58 harbouring the binary plasmid pC0301 containing rLuDGAT gene.
Vector Construction

Figure 8:
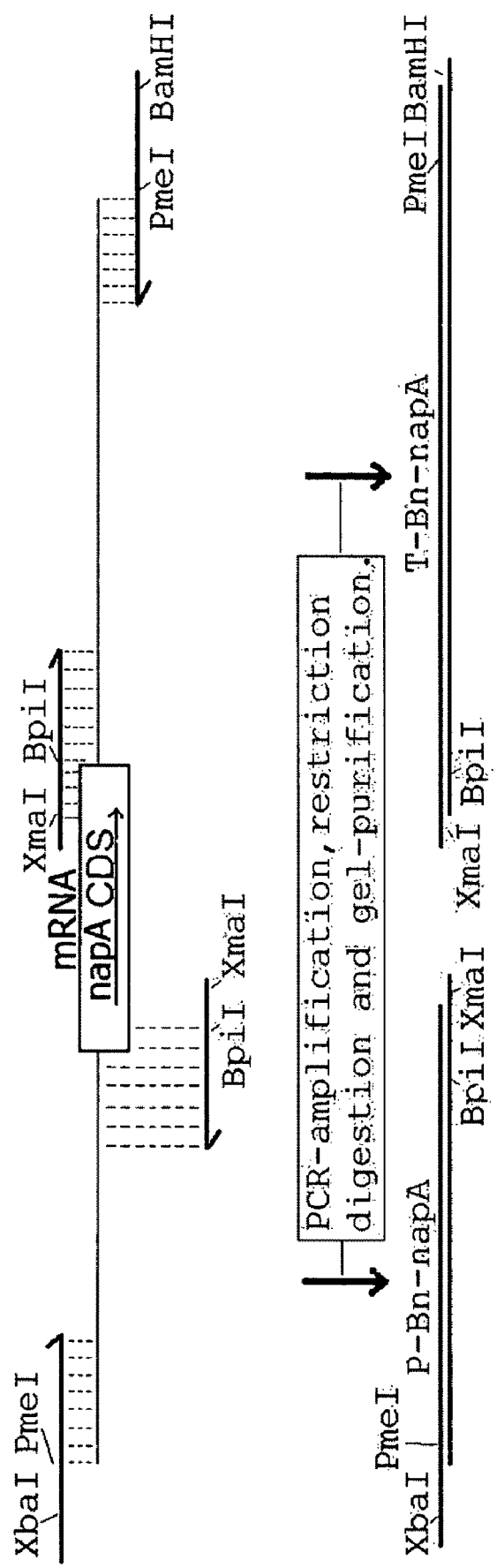
FIG. 8 is a schematic illustration of PCR-amplification of *Brassica napus* nap-A-promoter P-Bn-napA and *Brassica napus* napA-terminatorT-Bn-napA.
Figure 9:
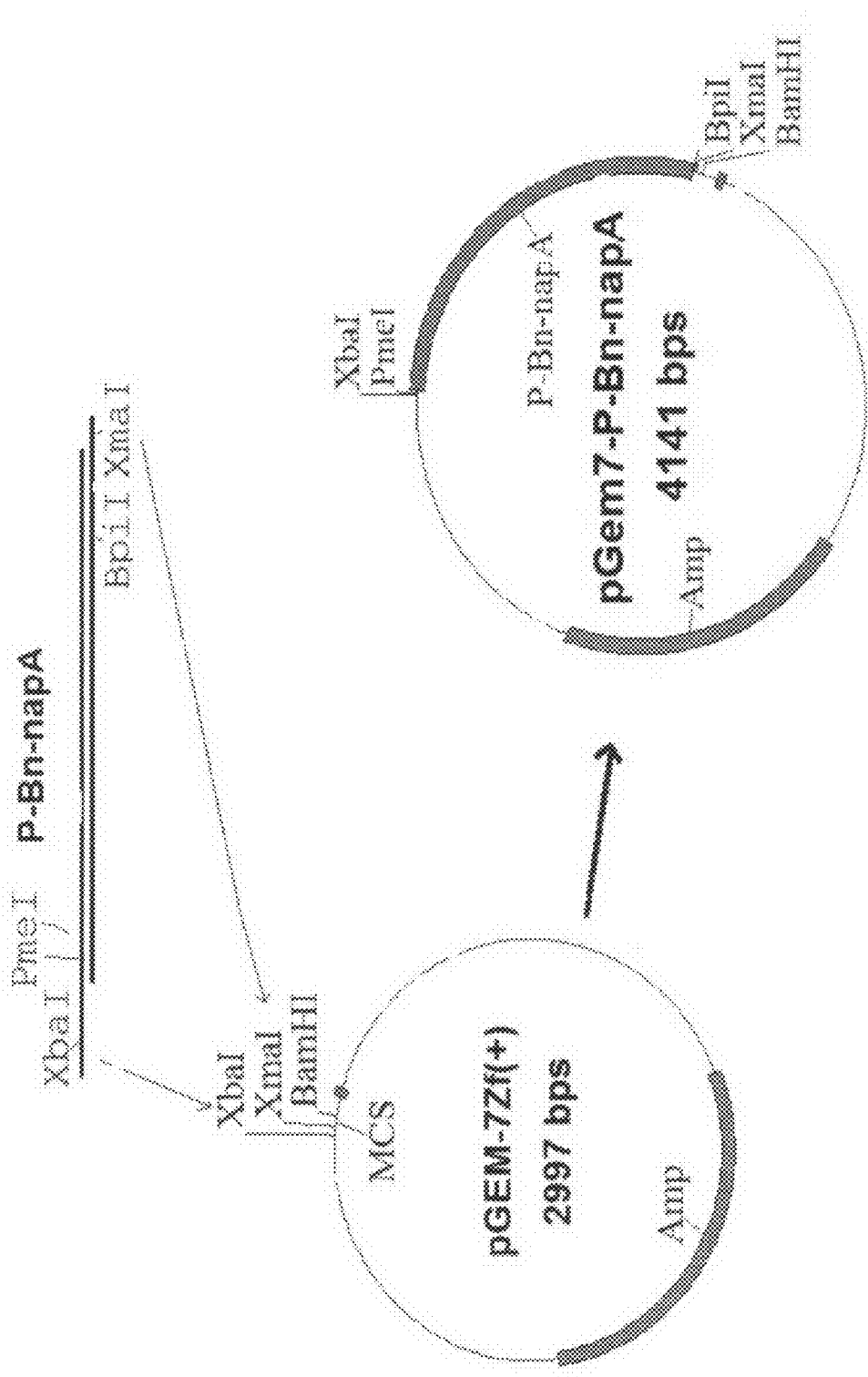
FIG. 9 illustrates construction of pGem7-P-Bn-napA construct.

*Brassica napus* napA-promoter (P-Bn-napA) is PCR-amplified from genomic DNA or from existing clone using high fidelity DNA polymerase. 5'-end of forward primer contains XbaI and PmeI restriction sites. 5'-end of reverse primer contains XmaI and BpiI restriction sites. P-Bn-napA amplification is shown in FIG. 8. The product is purified by EtOH precipitation, cut using XbaI and XmaI restriction enzymes, gel-purified and cloned into pGem-7Zf(+) vector, which is opened using XbaI and XmaI restriction enzymes, dephosphorylated with alkaline phosphatase and gel-purified. The construct is called pGem7-P-Bn-napA (FIG. 9).

Figure 10:
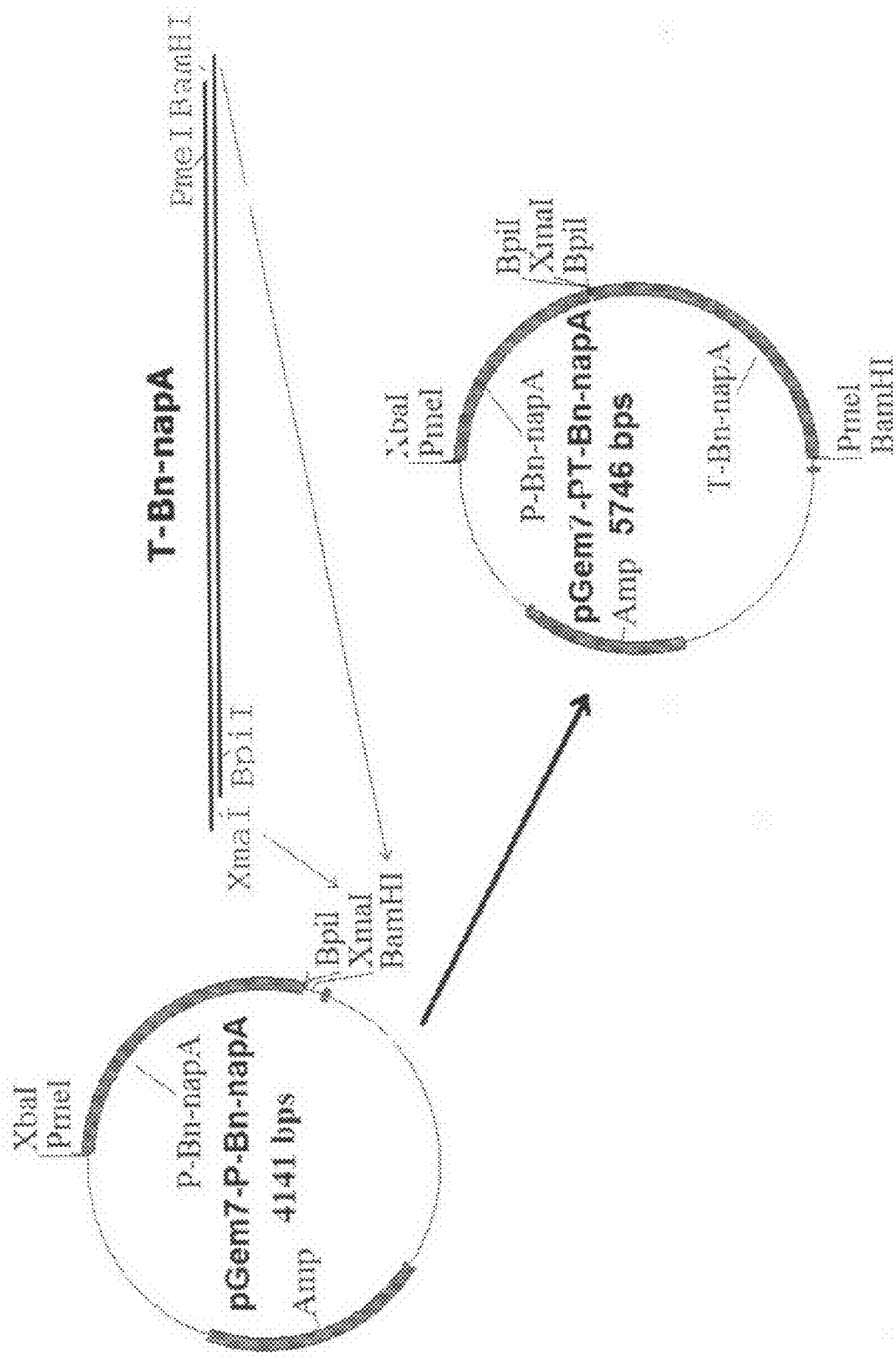
FIG. 10 illustrates construction of pGem7-PT-Bn-napA construct.

*Brassica napus* napA-terminator (T-Bn-napA: 3'-end of the gene following STOP-codon) is PCR-amplified from genomic DNA or from existing clone using high fidelity DNA polymerase. 5'-end of forward primer contains XmaI and BpiI restriction sites. 5'-end of reverse primer contains BamHI and PmeI restriction sites. T-Bn-napA amplification is shown in FIG. 8. The product is purified by EtOH precipitation, cut using BamHI and XmaI restriction enzymes, gel-purified and cloned into pGem7-P-Bn-napA, which is opened using BamHI and XmaI restriction enzymes, dephosphorylated with alkaline phosphatase and gel-purified. This construct is called pGem7-PT-Bn-napA and shown in FIG. 10.

Figure 11:
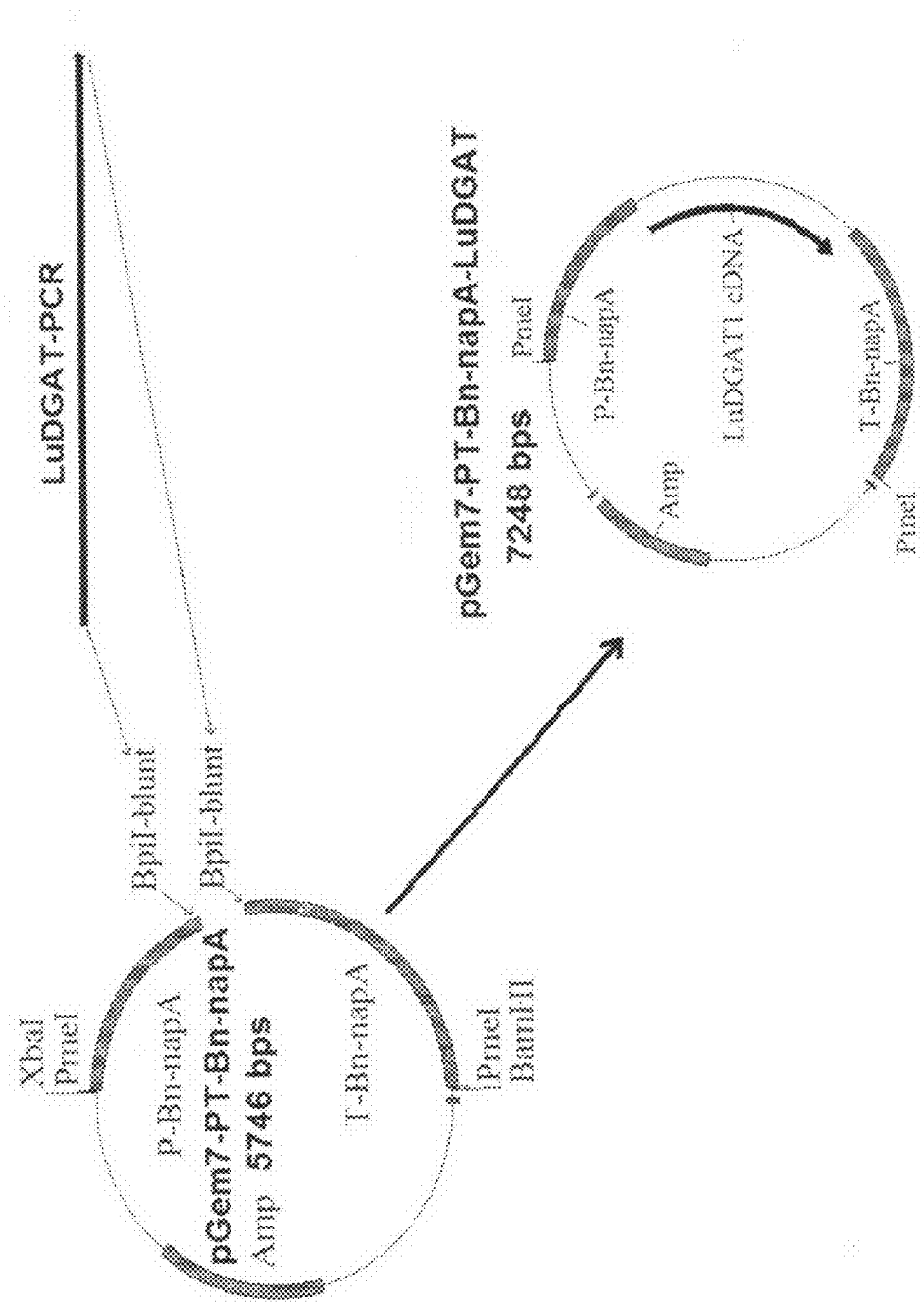
FIG. 11 illustrates construction of pGem-PT-Bn-napA-LuDFGAT construct.

Flax DGAT cDNA is cloned by PCR-amplification from cDNA, representing developing seed mRNA of flax or from existing cDNA clone using phosphorylated primers and high fidelity DNA polymerase leaving the ends of the product blunt. The product is gel purified and cloned into pGem7-PT-Bn-napA, which is opened using BpiI restriction enzyme, made blunt using Klenow fragment of *E. coli* DNA polymerase I, dephosphorylated and gel-purified. BpiI is an outside-cutter, which is used to cut so that the obtained ends contain no extra nucleotides when compared with native promoter and terminator. The construct is called pGem7-PT-Bn-napA-LuDGAT and shown in FIG. 11.

Figure 12:
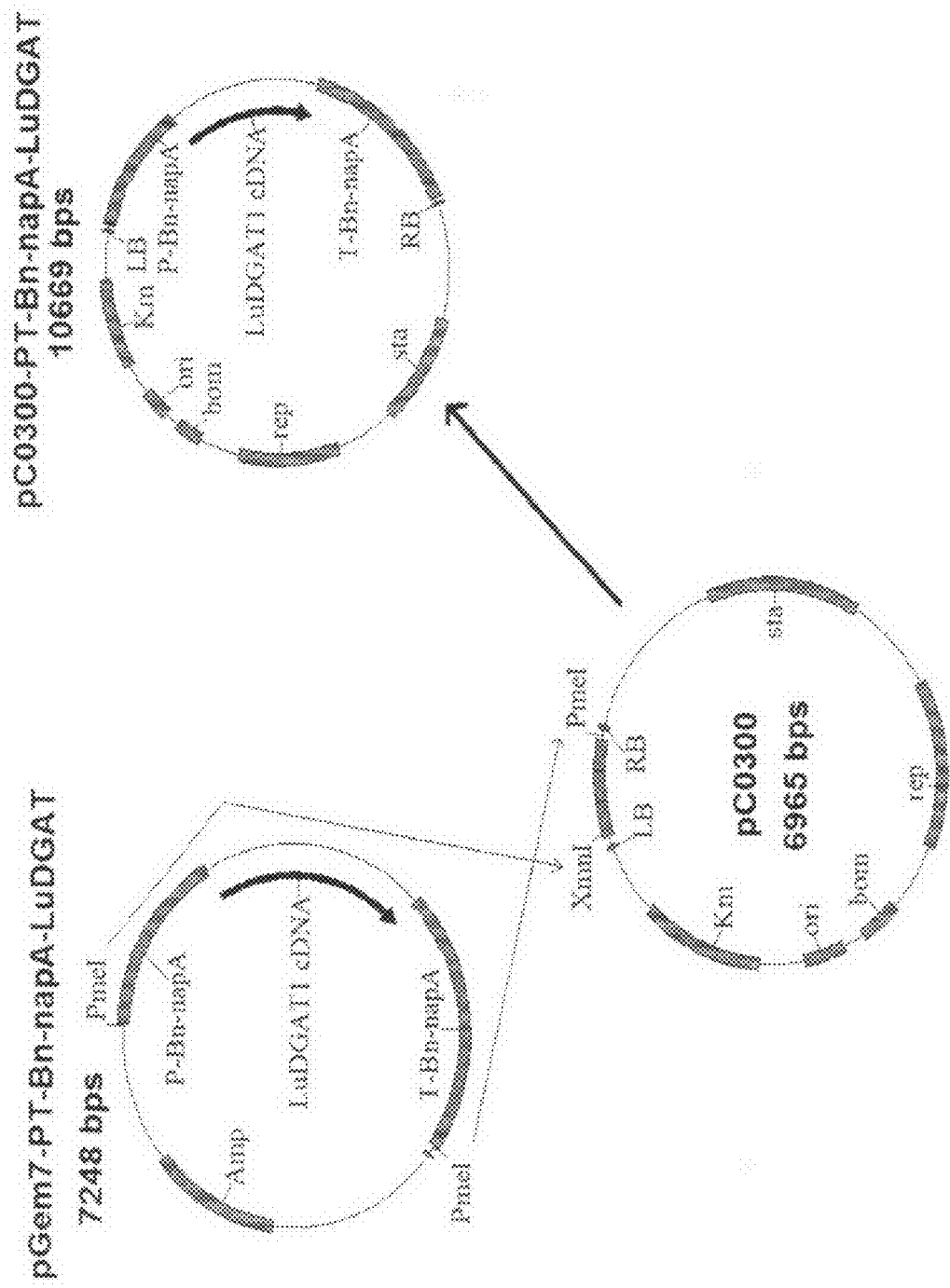
FIG. 12 illustrates construction of pC0300-PT-Bn-napA-LuDGAT construct.

The P-Bn-napA-LuDGAT-T-Bn-napA fragment is cut out from pGem7-PT-Bn-napA-LuDGAT using PmeI restriction enzyme, which leaves blunt ends and further cloned into pC0300 plant vector, which is opened using XmnI and PmeI restriction enzymes, dephosphorylated and gel-purified. pC0300 is a selection marker-free derivative of pCambia-1300. This construct is named pC0300-PT-Bn-napA-LuDGAT and shown in FIG. 12

The constructs are sequenced and electroporated into *Agrobacter thumefaciens* for plant transformation.
*Camelina sativa* Transformation The seeds of *Camelina sativa* plant grown in greenhouse are sterilized by immersing them in 70% ethanol for 1 min and then treating for 10 min with Na-hypochlorite solution (3% active Cl.sup.−) with an addition of Tween-20 (1 drop per 100 ml). After sterilization the seeds are washed three times in sterile water and placed on solid Murashige and Skoog (MS) agar medium (Murashige and Skoog, Physiol. Plant. 15:472-493, 1962) without sugars for germination. Sterilized seeds are germinated and grown 12 days on solid Murashige and Skoog (MS) medium without hormones Green leaves serve as a source of explants for transformation procedure.

*Agrobacterium tumefaciens* strain c58 carrying plasmid pC0301 containing rLuDGAT1, rLuDGAT2A or rLuDGAT2B gene are grown overnight at 28° C. with shaking in liquid YEB medium (Lichtenstein and Draper, Gene Engineering of Plants. In: Glover D M (ed.) DNA Cloning—A Practical Approach, vol. 2. Oxford IRL, Oxford, pp 67-119, 1985) supplemented with 50 mg/l kanamycin and 12.5 mg/l rifampicin. Subsequently an aliquot of the culture ({fraction (1/100)} v/v) is inoculated in fresh YEB medium supplemented with 50 mg/l kanamycin and 12.5 mg/l rifampicin and the bacteria are grown overnight with shaking. *Agrobacterium* culture of OD.sub.600=1.0 is used in the transformation experiments.

Narrow leaves of in vitro grown *Camelina sativa* plants are cut only across the leaf blade, whereas large leaves are additionally cut in half along the central vein. The leaf segments are cultivated for 24 hours on Murashige and Skoog (MS) 0.7% agar medium supplemented with 1.5 mg/l 6-benzylaminopurine (BAP) and 1.0 mg/l .alpha.-naphthaleneacetic acid (NAA). All the Murashige and Skoog (MS) culture medium are supplemented with 2% sucrose and all in vitro cultures are kept at temperatures of 25° C. (day) and 18° C. (night) under the photoperiod of 16 h. The explants are immersed for 1-3 min in Murashige and Skoog (MS) solution inoculated with a dilution (e.g. 1/10 v/v) of the overnight culture of *Agrobacterium tumefaciens*. Redundant liquid on the leaf segments is removed using filter paper and the explants are placed on Murashige and Skoog (MS) agar medium supplemented with auxin and cytokinin for co-cultivation with bacteria for 2 days.

The explants are washed with water containing Ticarcillin 200 mg/l. The surfaces of the explants are dried on filter paper and the explants were placed on Murashige and Skoog (MS) medium supplemented with hormones [1.5 mg/l 6-benzylaminopurine (BAP), 1.0 mg/l alpha-naphthaleneacetic acid (NAA)] and 200 mg/l Ticarcillin.

Leaf explants are transferred after 7 days to new MS medium containing 1.5 mg/l BAP and 100 mg/l Ticarcillin. After another 7 days the leaf explants are transferred to new MS medium containing 1.5 mg/l BAP and 200 mg/l Ticarcillin.

Shoots developed in this medium in 7 to 14 days are cut and placed on regular or half strength Murasghige and Skoog (MS) medium solidified with 0.7% agar and supplemented with 100 mg/l Ticarcillin and 0.3 mg/l NAA. After root formation the shoots are transferred to soil and transgenic plants are grown in greenhouse conditions. The presence of the rLuDGAT transgene is confirmed from transgenic plants using PCR assay and Northern blot.

Seeds of the transgenic *Camelina sativa* plants are collected and oil content and composition of the seeds is analyzed.

What is claimed is:

1. An isolated polynucleotide encoding a polypeptide comprising an amino acid sequence selected from:
   at least 300, contiguous residues of the amino acid sequence depicted in SEQ ID NO: 2 or of an amino acid sequence having at least 85% sequence identity therewith;
   wherein said polypeptide has diacylglycerol acyltransferase activity.

2. The isolated polynucleotide of claim 1, wherein the encoded polypeptide consists of the amino acid sequence depicted in SEQ ID NO: 2.

3. The isolated polynucleotide of claim 1, wherein the polynucleotide comprises the nucleotide sequence depicted in SEQ ID NO: 1 from nucleotide 57 to nucleotide 1580.

4. The isolated polynucleotide of claim 1, wherein the encoded polypeptide comprises an amino acid sequence having at least 90%, sequence identity to SEQ ID NO: 2.

5. A polynucleotide construct comprising a polynucleotide of claim 1 operably linked to a promoter expressible in bacterial, yeast, fungal, mammalian or plant cells.

6. A vector comprising a polynucleotide of claim 1.

7. The vector of claim 6, wherein the polynucleotide is operably linked to a seed specific promoter.

8. The vector of claim 7, wherein the promoter is *Brassica napus* napin promoter.

9. A microbial cell comprising a polynucleotide of claim 1.

10. The microbial cell of claim 9, wherein the cell is *Saccharomyces cerevisiae*.

11. A transgenic plant, plant cell, plant seed, callus, plant embryo, microspore-derived embryo, or microspore, produced by transformation with the polynucleotide of claim 1.

12. The transgenic plant, plant cell, plant seed, callus, plant embryo, microspore-derived embryo, or microspore of claim 11, which is selected from flax, canola, soybean, *Camelina sativa*, mouse-ear cress, castor, sunflower, linola, oats, wheat, triticale, barley, corn or *Brachypodium distachyon* plant, plant cell, plant seed, plant embryo, or microspore.

13. The transgenic plant of claim 12, wherein the plant is a *Camelina sativa* plant, comprising the polynucleotide of SEQ ID NO: 1 under control of *Brassica napus* napin promoter.

14. A method for producing oil, comprising the steps of:
   growing a transgenic plant according to claim 11; and
   recovering oil which is produced by the plant.

15. The method according to claim 14, wherein the plant is selected from flax, canola, soybean, *Camelina sativa*, mouse-ear cress, castor, sunflower, linola, oats, wheat, triticale, barley, corn or *Brachypodium distachyon* plant.

16. A method for producing a transgenic plant comprising the steps of:
   introducing into a plant cell or a plant tissue a polynucleotide of claim 1 to produce a transformed cell or plant tissue; and
   cultivating the transformed plant cell or transformed plant tissue to produce the transgenic plant.

17. The method of claim 16, wherein the polynucleotide is under control of seed specific promoter.

18. The method of claim 17, wherein the promoter is napin promoter.

19. The method of claim 16, wherein the plant is selected from flax, canola, soybean, *Camelina sativa*, mouse-ear cress, castor, sunflower, linola, oats, wheat, triticale, barley, corn or *Brachypodium distachyon* plant.

* * * * *